(12) United States Patent
Lazar et al.

(10) Patent No.: US 7,399,589 B2
(45) Date of Patent: Jul. 15, 2008

(54) IMMUNOLOGICAL DETECTION OF RNA:DNA HYBRIDS ON MICROARRAYS

(75) Inventors: James G. Lazar, Bethesda, MD (US); Joan M. Zakel, Ellicott City, MD (US); Christina M. Strange, Frederick, MD (US); Inna R. Williams, Rockville, MD (US); Attila T. Lorincz, North Potomac, MD (US); Abel De La Rosa, Alpharetta, GA (US)

(73) Assignee: Digene Corporation, Gaithersburg, MD (US)

( * ) Notice: Subject to any disclaimer, the term of this patent is extended or adjusted under 35 U.S.C. 154(b) by 530 days.

(21) Appl. No.: 10/735,082

(22) Filed: Dec. 11, 2003

(65) Prior Publication Data

US 2004/0180362 A1 Sep. 16, 2004

Related U.S. Application Data

(63) Continuation-in-part of application No. 09/707,178, filed on Nov. 6, 2000, now Pat. No. 6,686,151, which is a continuation-in-part of application No. 09/440,419, filed on Nov. 15, 1999, now Pat. No. 6,277,579, which is a continuation-in-part of application No. 09/020,067, filed on Feb. 6, 1998, now Pat. No. 5,994,079.

(51) Int. Cl.
C12Q 1/68 (2006.01)
C12P 21/08 (2006.01)
C07H 21/04 (2006.01)

(52) U.S. Cl. .................. 435/6; 530/388.1; 530/388.21; 536/24.3

(58) Field of Classification Search ....................... None
See application file for complete search history.

(56) References Cited

U.S. PATENT DOCUMENTS

| | | | |
|---|---|---|---|
| 4,563,417 A | 1/1986 | Albarella et al. |
| 4,732,847 A | 3/1988 | Stuart et al. |
| 4,743,535 A | 5/1988 | Carrico |
| 4,833,084 A | 5/1989 | Carrico |
| 4,851,330 A | 7/1989 | Kohne |
| 4,865,980 A | 9/1989 | Stuart et al. |
| 5,200,313 A | 4/1993 | Carrico |
| 5,244,797 A | 9/1993 | Kotewicz et al. |
| 5,412,087 A | 5/1995 | McGall et al. |
| 5,429,807 A | 7/1995 | Matson et al. |
| 5,455,170 A | 10/1995 | Abramson et al. |
| 5,510,270 A | 4/1996 | Fodor et al. |
| 5,668,005 A | 9/1997 | Kotewicz et al. |
| 5,827,661 A | 10/1998 | Blais |
| 5,981,179 A | 11/1999 | Lorinez et al. |
| 5,994,079 A | 11/1999 | De La Rosa et al. |
| 6,027,897 A | 2/2000 | Lorincz et al. |
| 6,043,038 A | 3/2000 | Sivaraja et al. |
| 6,232,068 B1 | 5/2001 | Linsley et al. |
| 6,686,151 B1 | 2/2004 | De La Rosa et al. |

FOREIGN PATENT DOCUMENTS

| | | |
|---|---|---|
| EP | 02 88737 A1 | 11/1988 |
| EP | 0 480 289 B1 | 3/1997 |
| GB | 2 279 954 A | 1/1995 |
| JP | 04-4267897 A | 9/1992 |
| WO | WO93 10263 A | 5/1993 |
| WO | WO 96/24694 | 8/1996 |
| WO | WO 97/10364 | 3/1997 |
| WO | WO 97/31256 | 8/1997 |
| WO | WO97 31256 A | 8/1997 |
| WO | WO99 29909 A | 6/1999 |
| WO | WO99 32654 A | 7/1999 |
| WO | WO99 36571 A | 7/1999 |
| WO | WO99 39001 A | 8/1999 |
| WO | WO99 40224 | 8/1999 |
| WO | WO 00 60116 A | 10/2000 |
| WO | WO 01/36681 | 5/2001 |

OTHER PUBLICATIONS

Blais, B.W., 1994 "Transcriptional Enhancement of the Listeria Monocytogenes PCR and Simple Immunoenzymatic Assay of the Product Using Anti-RNA:DNA Antibodies" Appl. Environ. Microbiol. 60:348-352.

Boguslawski et al., 1986 "Characterization of Monoclonal Antibody to DNA:RNA and Its Application to Immunodetection of Hybrids" J. Immunol. Methods 89:123-130.

(Continued)

Primary Examiner—John S. Brusca
(74) Attorney, Agent, or Firm—Morgan & Finnegan, LLP

(57) ABSTRACT

The present invention provides a hybridization method and kit for the detection and measurement of biological molecules. A test sample containing the biological molecules of interest is hybridized with an unlabeled or optionally a detectably-labeled complementary biomolecule to form a double-stranded hybrid immobilized to a solid phase. The immobilized hybrid may be detected with an entity which specifically recognizes an RNA:DNA hybrid, followed by analyses and quantification. Therefore, the present invention provides a method and kit to detect and measure biological molecules that is simple to use, highly specific, sensitive, and accurate for screening a plurality of biological molecules.

26 Claims, 23 Drawing Sheets

OTHER PUBLICATIONS

Coutlee et al., 1989 "Comparison of Colorimetric Fluorescent, and Enzymatic Amplification Substrate Systems in an Enzyme Immunoassay for Detection of DNA-RNA Hybrids" *J. Clin. Microbiol.* 27:1002-1007.

Coutlee et al., 1989 "Immunodetection of DNA with Biotinylated RNA Probes: A Study of Reactivity of a Monoclonal Antibody to DNA-RNA Hybrids" Anal. Biochem. 181:96-105.

Coutlee et al., 1989 "Nonisotopic Detection of RNA in an Enzyme Immunoassay Using a Monoclonal Antibody Against DNA-RNA Hybrids" *Anal. Biochem.* 181:153-162.

Coutlee et al., 1990 "Quantitative Detection of Messenger RNA by Solution Hybridization and Enzyme Immunoassay" J. Biol. Chem. 265:11601-11604.

Coutlee et al., 1991 "Immunodetection of DNA with Biotinylated RNA Probes: A Study of Reactivity of a Monoclonal Antibody to DNA-RNA Hybrids" Anal. Biochem. 198:217 (Published erratum).

Coutlee et al., 1991 "Detection of Transcripts of Human Papillomaviruses 16 and 18 in Cancer-derived Cell Line and Cervical Biopsies by Enzyme Immunoassay for DNA-RNA Hybrids Following Solution Hybridization" J. Clin. Microbiol. 29:968-974.

Ed M. Southern, "DNA chips: analyzing sequences by hybridization to oligonucleotides on a large scale," Mar. 1996, TIG, vol. 12, No. 3, pp. 110-115.

Lamourex et al., 1997 "Detection of Campylobacter jejuni in Food and Poultry Viscera Using Immunomagnetic Separation and Microtitre Hybridization," *J. Appl. Microbiol.* 83:641-651.

Lazar et al., 1999 "Hybrid Capture® : a Sensitive Signal Amplification-based Chemiluminescent Test for the Detection and Quantitation of Human Viral and Bacterial Pathogens," *J. Clin. Assay* 22:139-151.

Lennon et al. 1991 Hybridization analyses of arrayed cDNA libraries. Trends in Genetics, vol. 7, pp. 314-317.

Lockhart et al. "Expression monitoring by hybridization to high-density oligonucleotide arrays," Dec. 1996, Nature Biotechnology, vol. 14, pp. 1675-1680.

Maldonado-Rodriquez et al. "Hybridization of Glass-Tethered Oligonucleotide Probes to Target strands Preannealed with Labeled Auxiliary Oligonucleotides," 1999, Molecular Biotechnology, vol. 11, pp. 1-12.

Newman et al., 1989 "Solution Hybridization and Enzyme Immunoassay for Biotinylated DNA:RNA Hybrids to Detect Enteroviral RNA in Cell Culture" Mol. Cell Probes 3:375-382.

Stollar, B.D. and A. Rashtchian, 1987 "Immunochemical Approaches to Gene Probe Assays" Anal. Biochem. 161:387-394.

Tominaga et al., "Colorimetric ELISA measurement of specific mRNA on immobilized-oligonucleotide-coated microtiter plates by reverse transcription with biotinylated mononucleotides," 1996, Clinical Chemistry 42, No. 11, pp. 1750-1757.

Viscidi et al., 1989 "Monoclonal Antibody Solution Hybridization Assay for Detection of Human Immunodeficiency Virus Nucleic Acids" J. Clin. Microbiol. 27:120-125.

International Search Report for corresponding PCT Application No. PCT/US2004/041397.

Broker et al., "A Molecular Portrait of Human Papillomavirus Carcinogenesis", Cancer Cells, vol. 7, pp. 197-208, 1989.

De Villiers et al., "Classification of Papillomaviruses", Virology, vol. 324, pp. 17-27, 2004.

Hames & Higgins, Nucleic Acid Hybridisation: A Practical Approach (IRL Press Limited, Oxford, England. 1985).

Heilman et al., "Cloning of Human Papilloma Virus Genomic DNAs and Analysis of Homologous Polynucleotide Sequences", Journal of Virology, vol. 36, No. 2, pp. 395-407, Nov. 1980.

Hermanson, et al., eds. Immobilized Affinity Ligands (Academic Press, New York), 1992.

Higgins et al., "Transcription Patterns of Human Papillomavirus Type 16 in Genital Intraepithelial Neoplasia: Evidence for Promoter Usage within the E7 Open Reading Frame During Epithelial Differentiation", Journal of General Virology, vol. 73, pp. 2047-2057, 1992.

Howard et al., "Optimizing the Hybrid Capture II Human Papillomavirus Test to Detect Cervical Intraepithelial Neoplasia", Obstetrics and Gynecology, vol. 100, No. 5, Part 1, pp. 972-980, Nov. 2002.

Howley et al., "A Rapid Method for Detecting and Mapping Homology between Heterologous DNAs", Journal of Biological Chemistry, vol. 254, No. 11, pp. 4879-4883, Jun. 10, 1979.

Karlsen et al., "Use of Multiple PCR Primer Sets for Optimal Detection of Human Papillmavirus", Journal of Clinical Microbiology, pp. 2095-2100, Sep. 1996.

Law et al., "Conserved Polynucleotide Sequences Among the Genomics of Papillomavirus", Journal of Virology, vol. 32, No. 1, pp. 199-207, Oct. 1979.

Lorincz, A.T., "Molecular Methods for the Detection of Human Papillomavirus Infection", Obstetrics and Gynecology Clinics of North America, vol. 23, No. 3, pp. 707-730, Sep. 1996.

Mazzuli et al., "Multicenter Comparison of the Digene Hybrid Capture CMV DNA Assay (Version 2.0), the pp65 Antigenemia Assay, and Cell Culture for Detection of Cytomegalovirus Viremia", J. Clinical Microbiol., vol. 37, No. 4, pp. 958-963, Apr. 1999.

Park et al., "Physical Status and Expression of HPV Genes in Cervical Cancers", Gynecologic Oncology, vol. 65, pp. 121-129, 1997.

Stoler et al., "Human Papillomavirus Type 16 and 18 Gene Expression in Cervical Neoplasias", Human Pathology, vol. 23, No. 2, pp. 117-128, Feb. 1992.

Taylor, ed. Protein Immobilization: Fundamentals and Applications, M. Dekker, New York, 1991.

Arnold et al., "Assay Formats Involving Acridinium-Ester-Labeled DNA Probes," Clin. Chem., 35/8, 1588-1594 (1989).

Engelberg, N.C., Nucleic Acid Probe Tests for Clinical Diagnosis-Where Do We Stand? Features, vol. 57, No. 4, 183-186, 1991.

Gerry NP. et al., "Universal DNA Microarray Method for Multiplex detection of Low Abundance Point Mutations" Journal of Molecular Biology, vol. 292, pp. 251-262, Sep. 19, 1999.

Grunstein, et al., "Colony Hybridization: A Method for the Isolation of Cloned DNAs That Contain a Specific Gene," Proc. Natl. Acad. Sci. USA 72(10):3961-3965 (1975).

Guo, et al., "Direct Fluorescence Analysis of Genetic Polymorphisms by Hybridization With Oligonucleotide Arrays on Glass Supports," Nucleic Acids Res. 22(24):5456-5465 (1994).

Ishikawa, et al., "Enzyme-Labeling of Antibodies and Their Fragments for Enzyme Immunoassay and Immunohistochemical Staining," J. Immunoassay 4(3): 209-327 (1983).

Itakura, et al., "Synthesis and Use of Synthetic Oligonucleotides," Ann. Rev. Biochem. 53:323-356 (1984).

Johnstone, et al. "Immunochemistry in Practice", Blackwell Scientific Publications, 209-216 and 241-242 (1982).

Khrapko, et al., "Hybridization of DNA With Oligonucleotides Immobilized in Gel: A Convenient Method for Detecting Single Base Substitutions," Mol Biol (Mosk) (USSR) 25(3):718-730 (Translation Page No. 581-591) (1991).

Kitawaga, et al., "Comparison of Poly(A)-Poly(dT)and Poly(I)-Poly(dC) as Immunogens for the Induction of Antibodies to RNA-DNA Hybrids," Mol. Immunology 19(3):413-420 (1982).

Lesnick, et al., "Relative Thermodynamic Stability of DNA, RNA, and DNA-RNA Hybrid Duplexes: Relationship With Base Composition and Structure," Biochemistry 34:10807-10815 (1995).

Maniatis, et al., Molecular Cloning: A Laboratory Manual (New York, Cold Spring Harbor Laboratory, 1982).

Maskos et al., "Oligonucleotide Hybridizations on Glass Supports: A Novel Linker for Oligonucleotides Synthesis and Hybridisation Properties of Oligonucleotides Synthesized *In Situ*," Nucleic Acids Research 20:1679-1684 (1992).

McGraw et al., "Sequence-Dependent Oligonucleotide-Target Duplex Stabilities: Rules From Empirical Studies With a Set of Twenty-Mers," Biotechniques 8(6):674-678 (1990).

Means, et al., "Chemical Modifications of Proteins: History and Applications," Bioconj. Chem. 1:2-12 (1990).

Mierendorf, et al., "Sequencing RNA Transcripts Synthesized in Vitro From Plasmids Containing Bacteriophage Promoters," Methods. Enzymol. 152:563-566 (1987).

Narang, et al., "Chemical Synthesis of Deoxyoligonucleotides by the Modified Triester Method," Methods Enzymol. vol. 65, Chapter 61, pp. 610-620 (1980).

Pease, et al., "Light-Generated Oligonucleotide Arrays for Rapid DNA Sequence Analysis," Proc. Natl. Acad. Sci. USA 91(11):5022-5026 (1994).

Rychlik, et al., "Optimization of the Annealing Temperature for DNA Amplification in vitro," Nucleic Acids Res. 18(21):6409-6412 (1990).

Sambrook et al., Molecular Cloning: A Laboratory Manual, 2nd Edition (Cold Spring Harbor Laboratory Press, Cold Spring Harbor, N.Y.) 1989) Chapters 5, 6).

Schena, et al., "Quantitative Monitoring of Gene Expression Patterns With a Complementary DNA Microarray," Science 270:467-470 (1995).

Southern E. M., "Detection of Specific Sequences Among DNA Fragments Separated by Gel Electrophoresis," J. Mol. Biol. (1975) 98, 503-517.

Stimpson, et al., "Real-Time Detection of DNA Hybridization and Melting on Oligonucleotide Arrays by Using Optical Wave Guides," Proc. Natl. Acad. Sci. USA 98:6379-6383 (1995).

Stuart, et al., "Location of the 18/28S Ribosomal RNA Genes in Two Hawaiian Drosophila Species by Monoclonal Immunological Identification of RNA-DNA Hybrids in situ," Proc. Natl. Acad. Sci. USA 78(6):3751-3754 (1981).

Syvanen, et al., "Fast Quantification of Nucleic Acid Hybrids by Affinity-Based Hybrid Collection," Nucleic Acids Res. 14(12):5037-5048 (1986).

Viscidi et al., 1989 "Monoclonal Antibody Solution Hybridization Assay for Detection of Human Immunodeficiency Virus Nucleic Acids" J. Clin. Microbiol. 27:120-125.

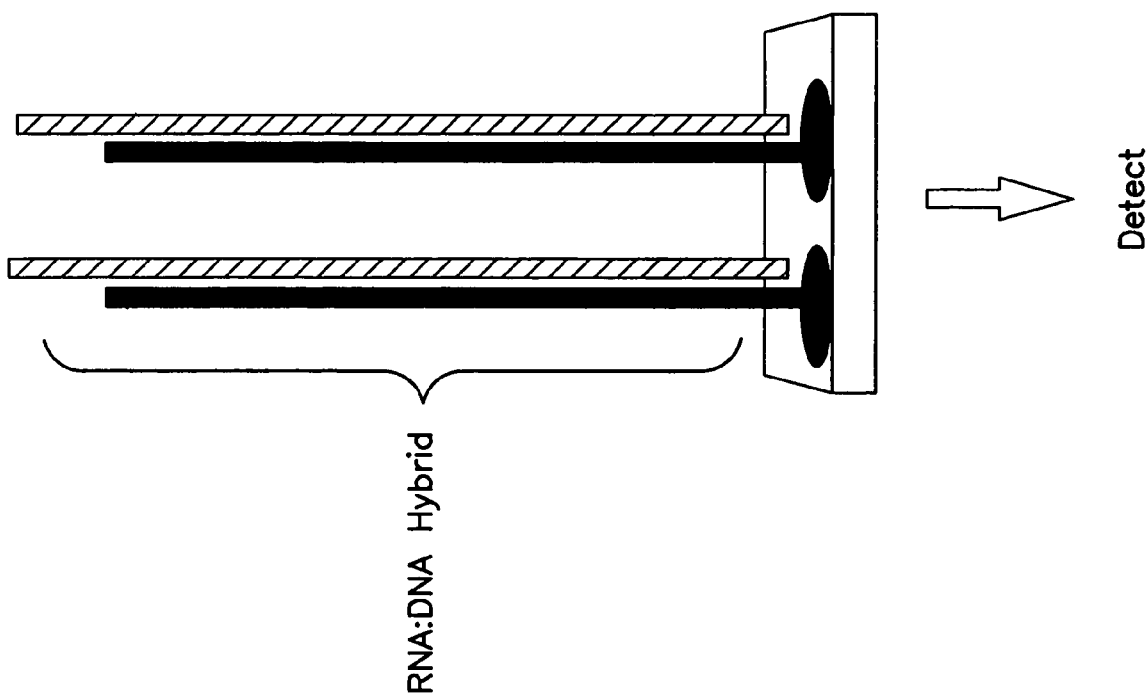

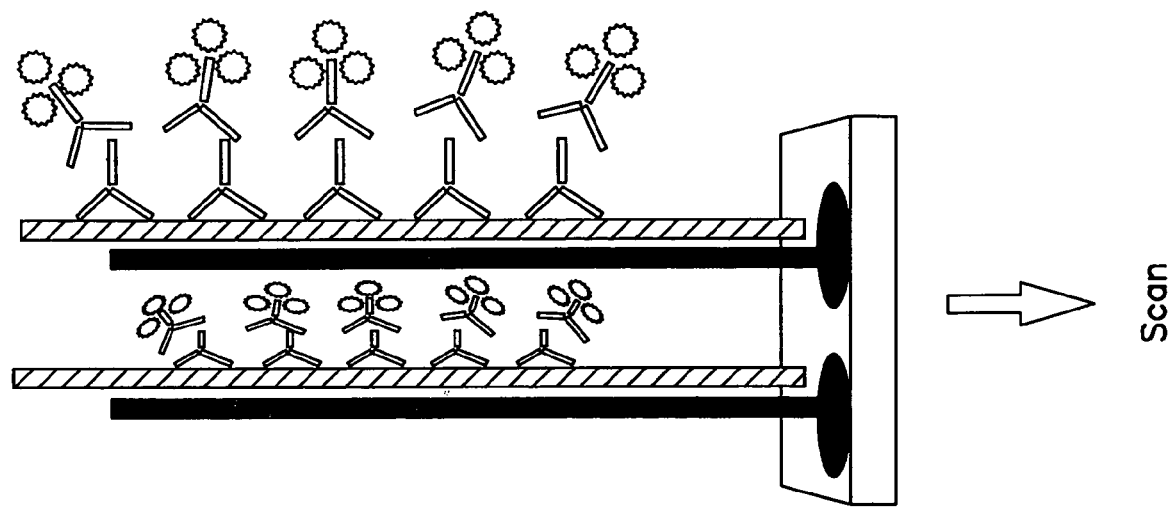

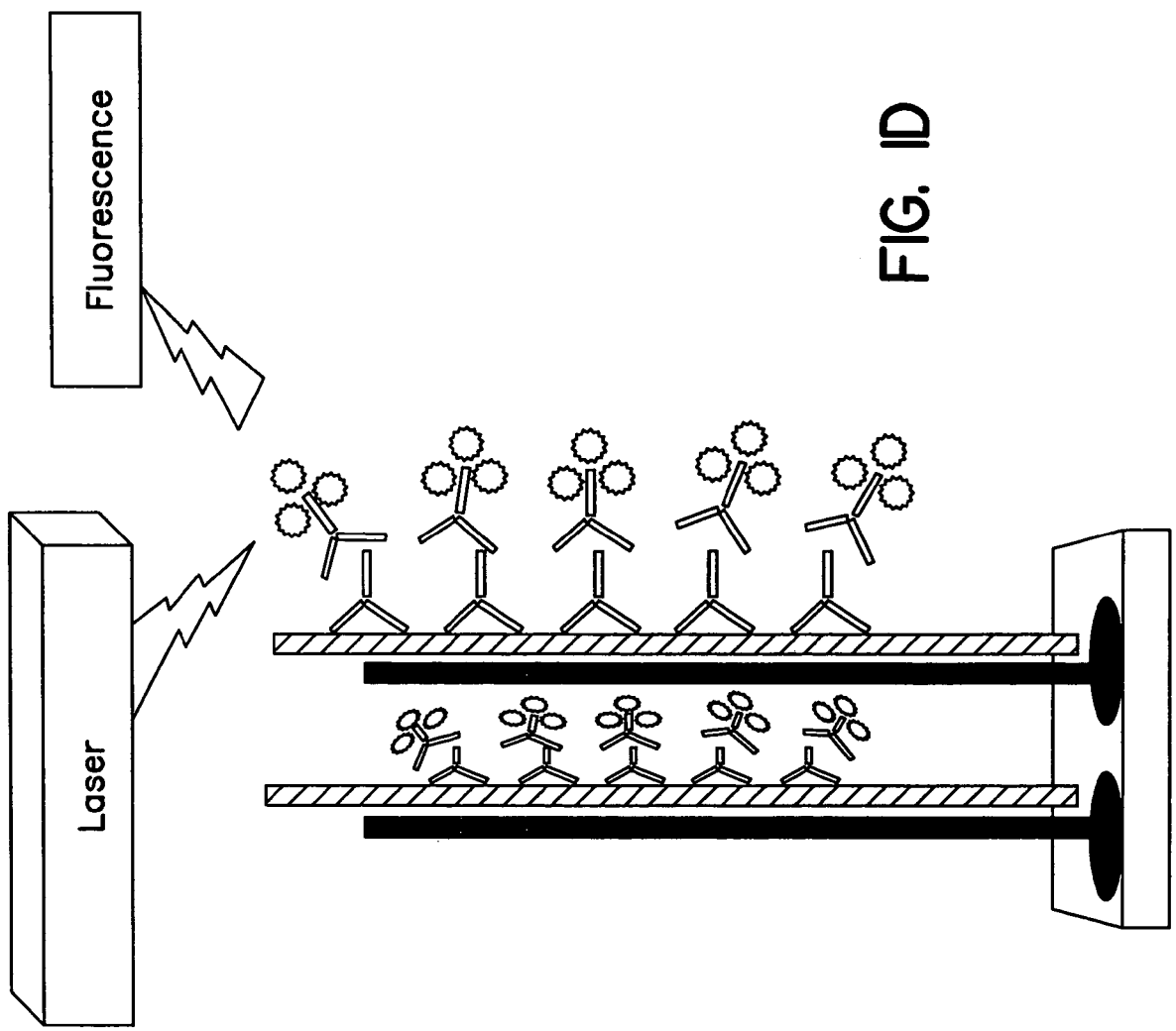

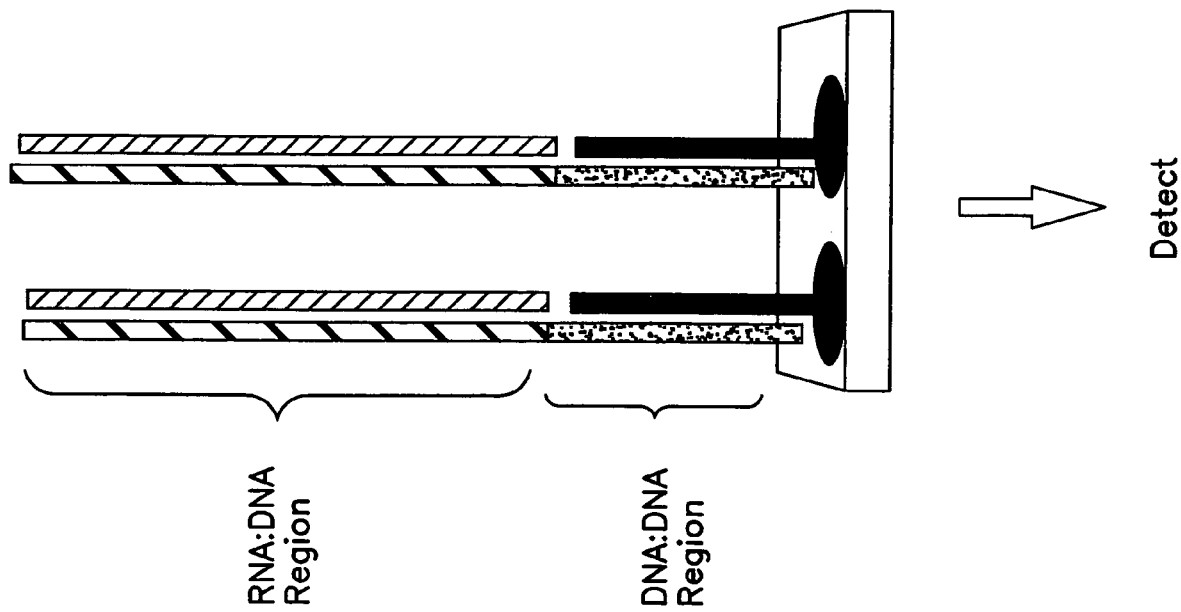

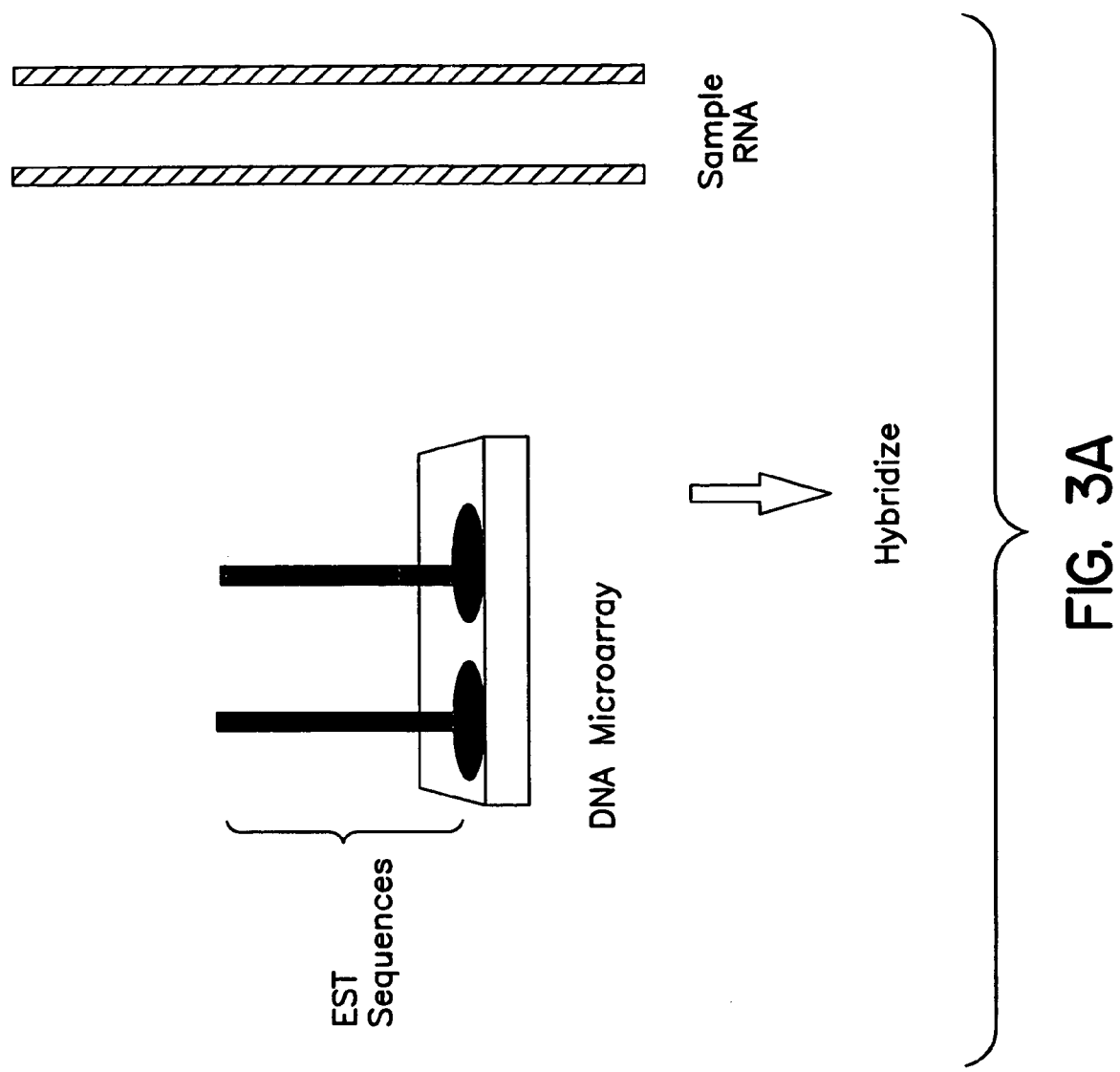

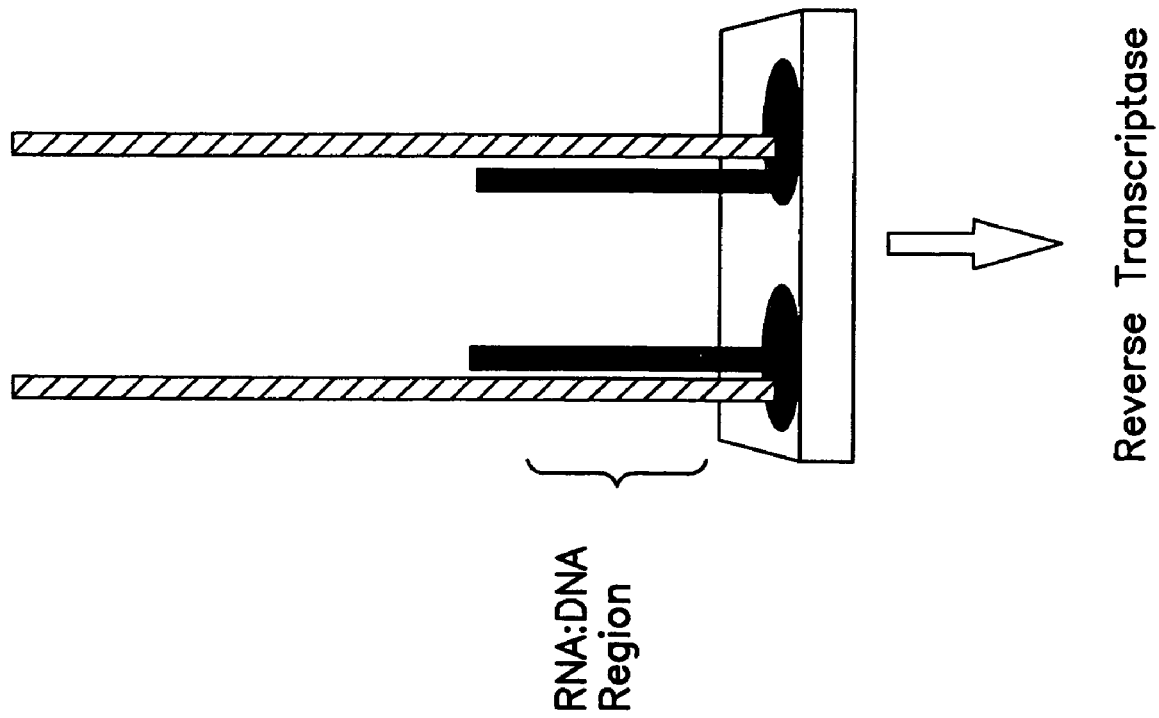

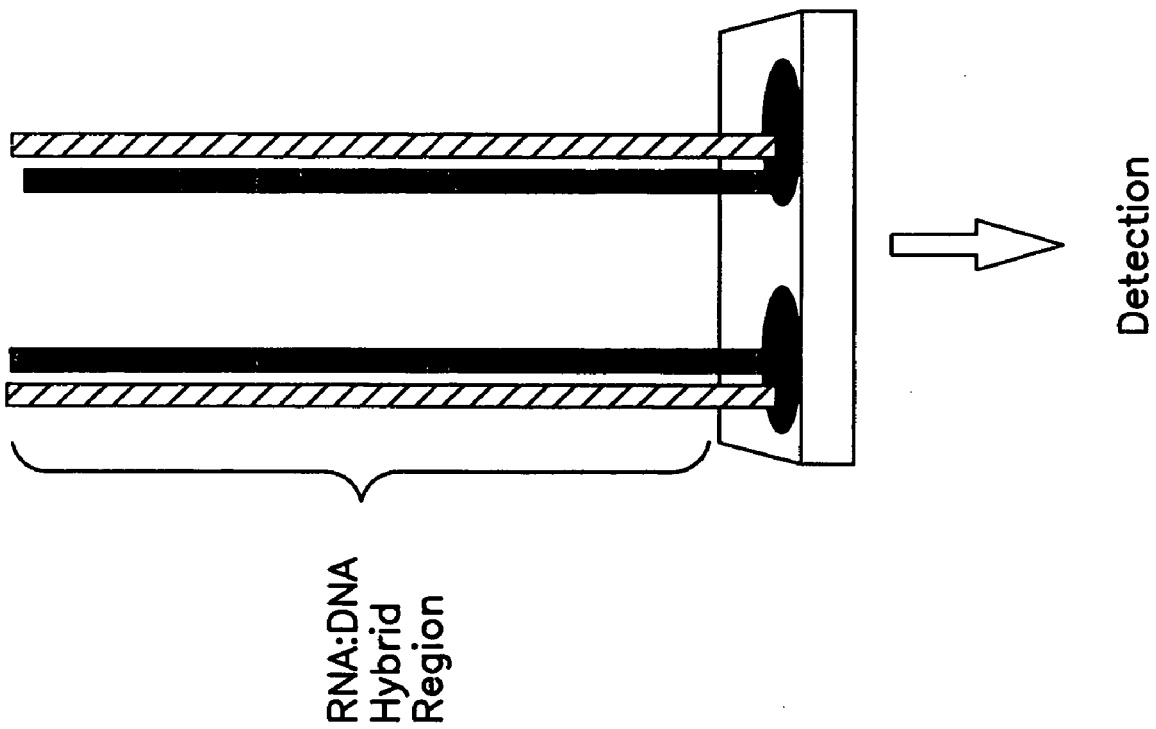

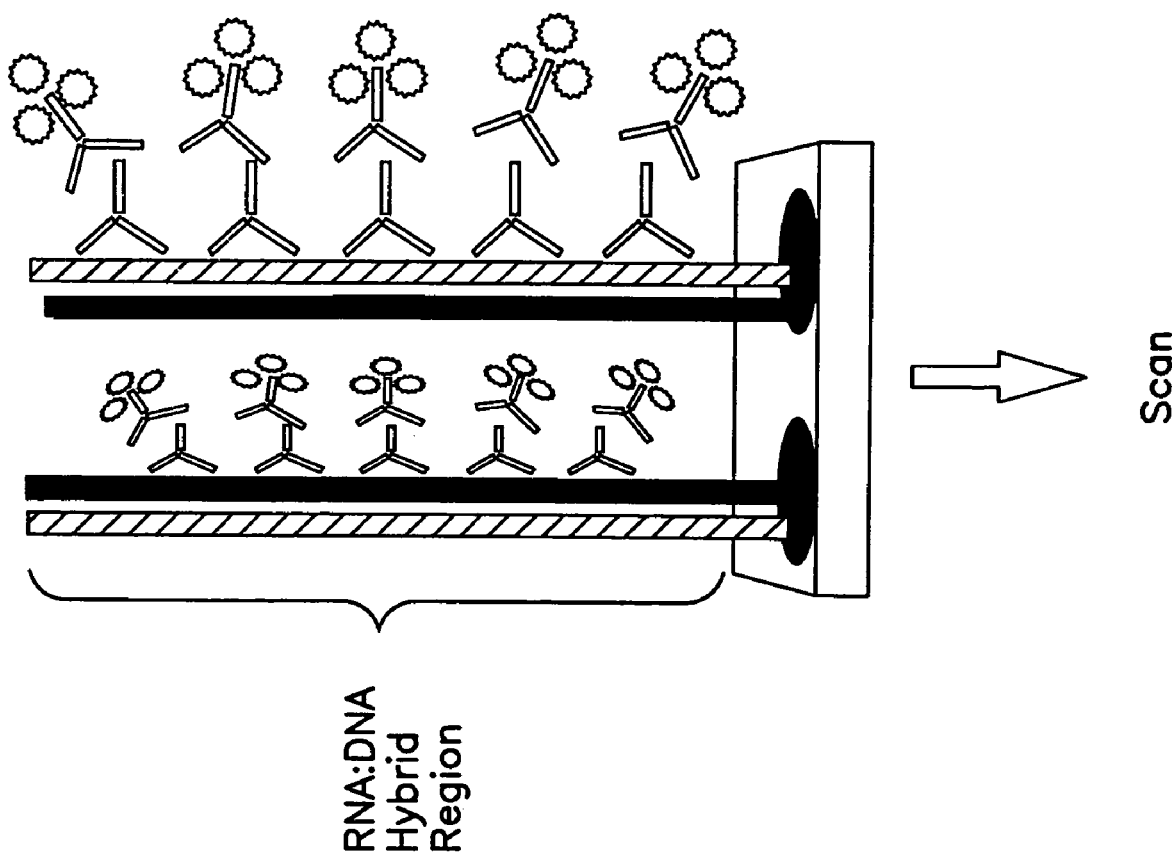

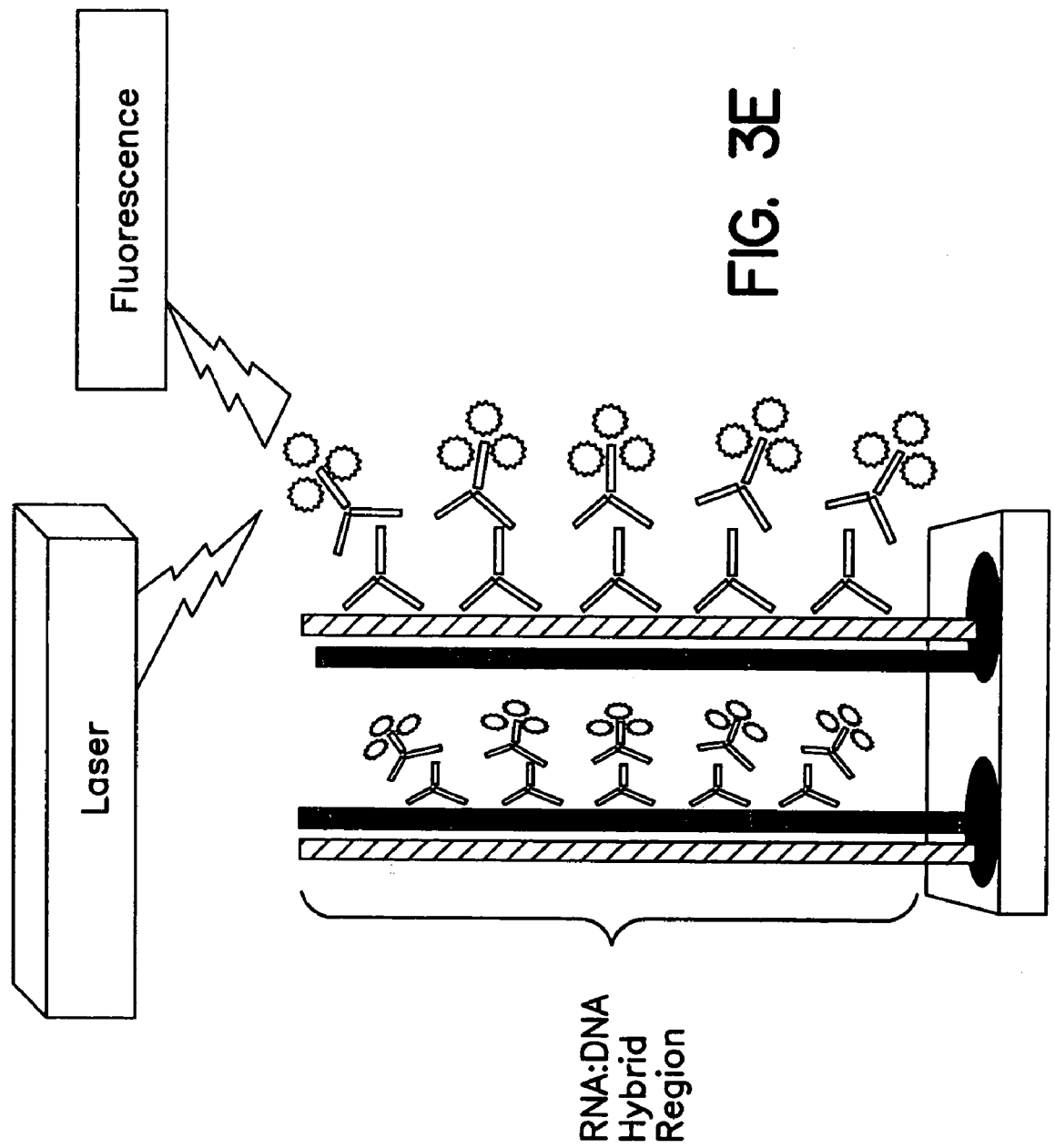

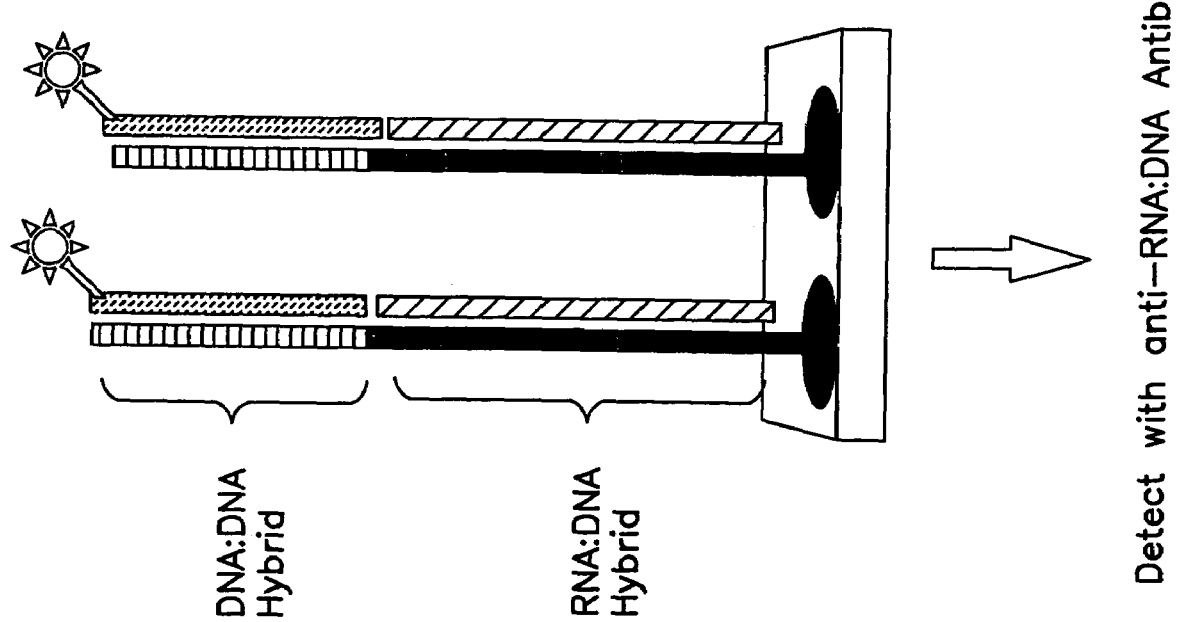

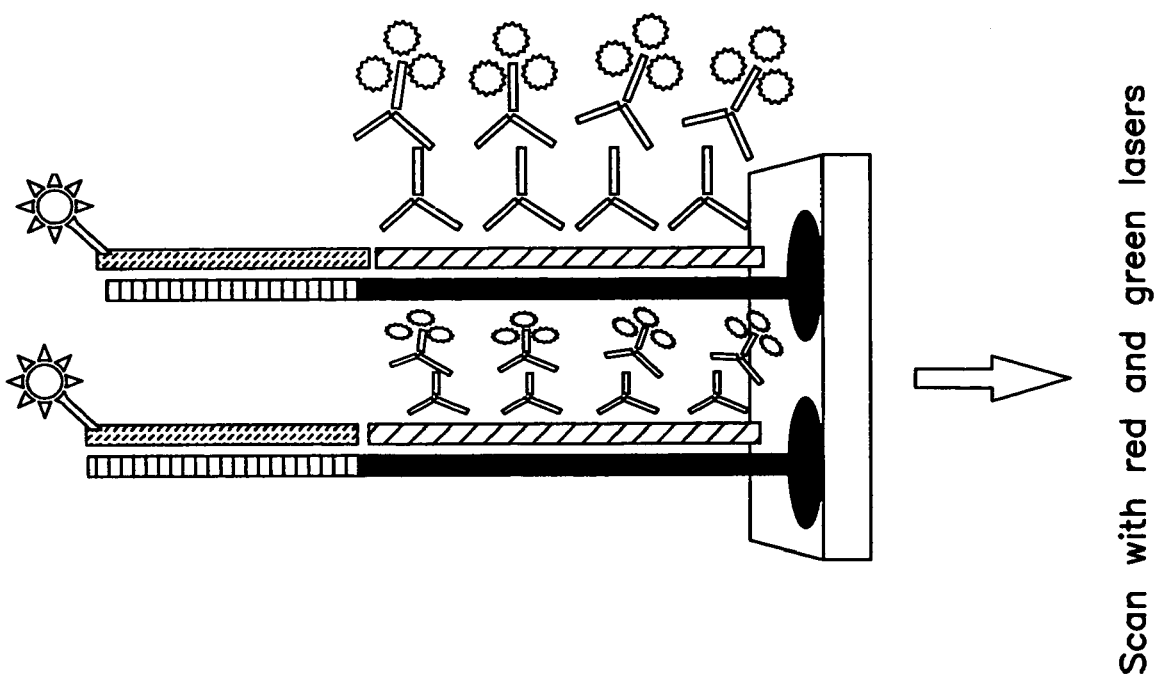

Normalize Signal from RNA (green) with Signal from DNA (red)

(hybridization may be simultaneous or sequential depending on the DNA sequence length)

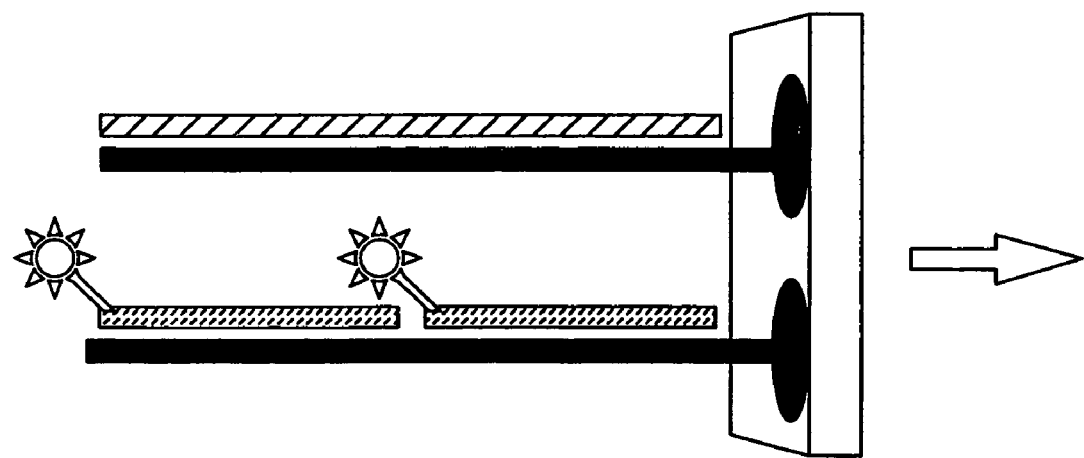

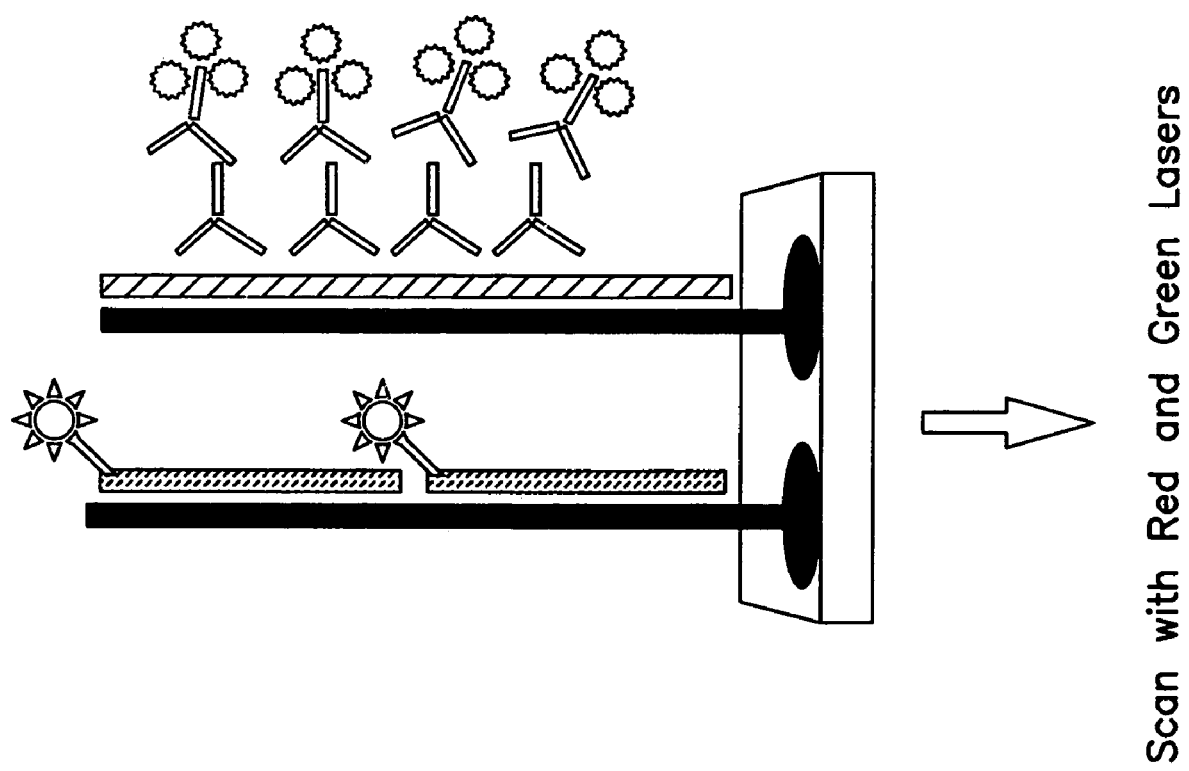

Normalize Signal from RNA (green) with Signal from DNA (red)

IMMUNOLOGICAL DETECTION OF RNA:DNA HYBRIDS ON MICROARRAYS

This application is a continuation-in-part application of U.S. application Ser. No. 09/707,178 filed Nov. 6, 2000 now U.S. Pat. No. 6,686,151 by Lazar, et al., entitled "Immunological Detection Of RNA:DNA Hybrids On Microarrays," which is a continuation-in-part of application Ser. No. 09/440,419, now U.S. Pat. No. 6,277,579, filed Nov. 15, 1999 by Lazar, J. G. et al., entitled "Direct Detection of RNA Mediated by Reverse Transcriptase Lacking RNAse H Function", which is a continuation-in-part of application Ser. No. 09/020,067, now U.S. Pat. No. 5,994,079, filed Feb. 6, 1998, entitled "Direct Detection of RNA Mediated by Reverse Transcriptase Lacking RNase H Function," by Abel De La Rosa and Clayton D. Collier.

FIELD OF THE INVENTION

The present invention is in the general field of detection of biological molecules, including DNA, RNA, protein and the like, and specifically in the field of detection of RNA:DNA hybrids on a solid phase, as further described herein, using a hybridization assay.

BACKGROUND OF THE INVENTION

The RNA or DNA for many genes, including those associated with disease states, and microorganisms and viruses have been isolated and sequenced. Nucleic acid probes based on such sequences are currently available to identify a large number of genes and infections. Nucleic acid probes are detectable nucleic acid sequences that hybridize to complementary RNA or DNA sequences in a test sample. Detection of the probe indicates the presence of a particular nucleic acid sequence in the test sample for which the probe is specific. In addition to aiding scientific research, nucleic acid probes may be used to detect the presence of viruses and microorganisms such as bacteria, yeast and protozoa as well as genetic mutations linked to specific disorders in patient samples.

Grunstein, et al, *Proc. Natl. Acad. Sci. USA* 72:3961 (1975) and Southern, *J. Mol. Biol.* 98:503 (1975) describe hybridization techniques using radiolabeled nucleic acid probes. Nucleic acid hybridization probes have the advantages of high sensitivity and specificity over other detection methods and do not require a viable organism. Hybridization probes are often labeled with a radioactive substance that may be easily detected.

The existing hybridization techniques that utilize radioisotopes to label probes introduce additional expenses caused by the high costs of disposal of radioactive waste products and the need for monitoring personnel and the workplace for contamination. In addition, the short half-life of radioactive compounds such as $^{32}P$ requires that radioactive probes be produced frequently. Radioactive nucleic acid hybridization is therefore discouraged in commercial areas such as clinical diagnosis.

Probes have been indirectly labeled in an attempt to avoid the problems associated with direct radioactive labeling. One common method of indirect labeling is to attach biotin, a small vitamin, to the nucleic acid probe using a chemical or enzyme technique. Following hybridization to the specific nucleic acid, the biotin is detected by reaction with streptavidin, a protein that binds biotin tightly and has been labeled with an enzyme or fluorochrome. Bound biotin-streptavidin complex may be detected by reaction with color-producing substrates and the fluorochrome may be seen when reacted with incident light of appropriate wavelength. However, indirect labeling of hybridization probes with biotin or other haptens often increases the "hydrophobicity" of the probe. The probe tends to interact non-specifically with materials other than the complementary nucleic acid target, leading to high background. The biotin label increases non-specific binding, which leads to high background, thereby reducing sensitivity and increasing the likelihood of a false-positive result. Indirect labeling is also less sensitive than direct labeling because the labeling density is limited; only a small fraction of the bases are labeled giving a limiting number of sites for signal generation. An increase in the labeling density of a probe leads to increased non-specific binding, higher background, and ultimately, failure of the probe to hybridize with its target due to the interference of the hapten with base pairing. Indirectly labeled probes are therefore not well suited to clinical diagnosis because of its inaccuracy and false positive results.

Hybridization of a probe to the specific nucleic acid sequences has been detected with the use of an intercalating agent such as acridine orange or ethidium bromide as described in U.S. Pat. No. 4,563,417 to Albarella et al. The intercalating agent becomes inserted between hybridized base pairs of probe and sample nucleic acids and causes the tertiary structure of the helix to unwind. An antibody specific for the newly formed antigenic determinant created by the intercalating agent and the unwound helix is detected by conventional means. This method lacks selectivity for the target hybrids because intercalating agents fail to recognize specific sequences. Furthermore, the antibodies recognize only the intercalating agent/nucleic acid complex, but do not detect a specific sequence. Therefore, additional selection or purification steps are required to prevent non-specific signal, making this time consuming and labor intensive approach poorly suited for clinical diagnosis Hybridization of the probe to the specific nucleic acid sequences may also be detected with the aid of an antibody specific for a labeled probe as described in U.S. Pat. No. 4,743,535 to Carrico. The probe is labeled with a detectable substance such as flavin adenine dinucleotide (FAD) or a fluorescent agent. An antibody specific for the labeled probe, after it has hybridized to the specific nucleic acid sequence, is detected by a biochemical reaction. This method of detection also creates non-specific binding and the likelihood of false-positive results and is not well suited for clinical screening.

Attempts have been made to increase the sensitivity of nucleic acid assays by target amplification. Methods of amplifying nucleic acid sequences are commercially available. These methods include the polymerase chain reaction (PCR), the ligation amplification reaction (LCR), and the transcription based amplification reaction (TMA). PCR technology is described in *PCR Protocols A Guide to Methods and Applications* by Michael A. Innis, David H. Gelfand, John J. Sninsky and Thomas J. White, pp. 39–45 and 337–385 (Academic Press, Inc., Harcourt Brace Jovanovich, Publishers, 1990). PCR technology is also described by Marx, J. L., *Science* 140:1408–1410 (1988) and in U.S. Pat. Nos. 4,683, 195 and 4,683,202, to Mullis. Ligation amplification reaction is described by Wu, D. Y and Wallace, R. B, *Genomics* 4:560–569 (1989) and Barringer, K. J., et al., *Gene* 89:117–122 (1990). Transcription based amplification reaction is described by Kwoh, D.Y., et al., *Proc. Natl. Acad. Sci. USA* 86:1173–1177 (1989). These methods have the advantages of high sensitivity, but the disadvantages of having a lengthy, tedious, and expensive sample preparation, being prone to false-positive results from reaction product contamination, and having the inability to accurately quantify the initial amount of target nucleic acids. Amplification reaction products are most often detected by a hybridization assay.

The degree of sensitivity achieved in assays for the detection of nucleic acid molecules, either RNA or DNA, in a sample is generally lower for RNA than DNA because RNA is subject to degradation by endogenous RNAses in the sample, resulting in less RNA available for detection. In addition, background interference caused by contaminants in the sample is difficult to eliminate without causing further degradation of the target nucleic acid, such as RNA.

Hybridization assays for the detection of nucleic acid molecules, i.e. RNA, have been developed. For example, a hybridization protection assay for RNA is commercially available from Gen-Probe Inc. (San Diego, Calif.). The hybridization protection assay employs a single-stranded nucleic acid probe linked to an acridinium ester, as described by Engleberg, N. C., ASM News 57:183–186 (1991), Arnold et al. Clin. Chem. 35:1588–1594 (1989) and U.S. Pat. No. 4,851,330. Hybridization of the probe to a target RNA molecule protects the acridinium ester bond from heat hydrolysis so that the detected chemiluminescent signal is proportional to the amount of target RNA in the sample. The sensitivity of this protection assay is limited by background luminescence caused by non-hybridized probe.

Polyclonal and monoclonal antibodies and other similar entities are commonly used for detection purposes. Specifically, polyclonal antibodies recognize a plurality of epitopes, while monoclonal antibodies only recognize one specific epitope. Monoclonal antibodies which detect RNA:DNA hybrids are currently available. Polyclonal antibodies which detect RNA:DNA hybrids have been prepared, although, generally, they have not been as specific as the monoclonal antibodies, which are designed to bind to a specific epitope.

Monoclonal antibodies to RNA:DNA hybrids are now available. U.S. Pat. No. 4,732,847 to Stuart et al. and the publication of Stuart et al., Proc. Natl. Acad. Sci. USA 78:3751 (1981) describe a method of hybridization detection of specific nucleic acid sequences on a solid surface involving a monoclonal antibody specific for a poly(A)-poly(dT) duplex. In Stuart, annealing DNA or RNA sequences complementary to the sequence of interest forms RNA:DNA hybrids. Stuart specifically teaches against the use of polyclonal antibodies because with polyclonal antibodies, one cannot preclude significant binding to single- or double-stranded nucleic acids. Further, unlike the present invention described herein, Stuart does not contemplate the advantages of polyclonal antibodies for arrays of very short oligomers on glass or silicon chips. In addition, Stuart does not contemplate microarrays, especially high-density arrays on glass slides or silicon chips. Nor does Stuart disclose attaching a nucleic acid probe to the surface of a solid phase. Instead, Stuart fixes a sample polynucleotide to a surface, while probe (e.g., a predetermined nucleotide sequence) is present in the liquid phase. In view of the foregoing, the present invention provides significant benefits and advantages to the art.

Boguslawski et al., J. Immunol. Methods 89:123–130 (1986) developed a hybridization assay using anti-hybrid coated polystyrene beads isolated on filter paper in an attempt to reduce non-specific binding and avoid complicated washing procedures. A monoclonal antibody specific for RNA:DNA hybrids secreted by hybridoma HB 8730, is disclosed in U.S. Pat. No. 4,833,084 to Carrico et al. In Carrico, RNA:DNA hybrids formed by specific reannealing of a probe polynucleotide and the sequence of interest can be sensitively and specifically detected by binding to the monoclonal antibodies.

Microarrays refer to an orderly arrangement of distinct biological molecules, including RNA, DNA, protein, or the like, arrayed or immobilized to a solid substrate. These microarrays of binding agents, such as oligonucleotides and probes, have become an increasingly important tool in the biotechnology industry and related fields. Microarrays comprising a plurality of binding agents or elements are immobilized onto the surface of a solid support in an orderly fashion or pattern, find use in a variety of applications, including drug screening, nucleic acid sequencing, mutation analysis, and the like. Elements as used herein in a microarray context, refer to hybridizable nucleic acid sequences, oligonucleotides, primers, probes, and/or amino acid sequences arranged in a distinct and identifiable manner on the surface of a substrate. Detection of biological molecules through the use of microarrays is beneficial for analyzing numerous samples and biological molecules, reducing the amount of sample required for analysis, decreasing experimental variability, decreasing sample preparation time, confirming results, and for decreasing costs of such analysis.

Currently, one of the primary uses of microarrays is to measure gene expression in biological samples. Gene expression measurements include detecting the presence or absence of mRNA or measuring increased or decreased concentrations of mRNA. In order to detect hybridization and to measure gene expression by conventional methods, however, the sample must first be purified and labeled. Two common techniques for purifying and labeling the sample are: 1) RNA amplification, labeling, and hybridization, and 2) cDNA labeling and hybridization. The amplification part of the first technique is described in U.S. Pat. Nos. 5,716,785 and 5,891,636 issued in 1998 and 1999, respectively, to Van Gelder et al. Highly purified total RNA or mRNA is used, which is an expensive and tedious time-consuming procedure. An oligo-dT primer is also used to reverse-transcribe the poly A-tailed mRNA into an anti-sense single-stranded cDNA. The oligo-dT further contains the sequence for T7 RNA polymerase on the 5 prime end of the dT sequences. After reverse transcription, a combination of RNAse H, DNA ligase, and DNA polymerase are used to generate a double stranded cDNA. Because the original RT primer contained a T7 RNA polymerase promoter, the double-stranded cDNA contains a full T7 RNA promoter. The double-stranded cDNA is then used as a template for T7 RNA polymerase. Approximately 100–1000 additional copies of RNA are generated from each copy of cDNA. During the transcription process, labeled nucleotides are incorporated into the transcribed RNA. Labeled RNA is then hybridized to the DNA microarray forming labeled RNA: DNA hybrids. Fluorescent labels may be detected directly while indirect labels may be detected after reaction with a secondary binding agent.

A second sample preparation technique produces and measures labeled cDNA. In this technique total RNA or mRNA is purified from the biological sample. An oligo-dT primer is used to reverse-transcribe the poly-A tailed mRNA into an anti-sense single-stranded cDNA. During the reverse-transcription, labeled nucleotides are incorporated into the nascent DNA strand. After synthesis, the RNA strand is destroyed. The labeled cDNA strand is then hybridized to the microarray. If the nucleotides were labeled with fluorescence, then the hybrids are visualized directly with a fluorescence array scanner. If the nucleotides were labeled with biotin, then the microarray is first reacted with labeled streptavidin and then scanned.

The disadvantages of both of these techniques are several fold. Firstly, both require a large quantity of highly purified nucleic acids (i.e. RNA or DNA). Purification requires additional steps which are time consuming and labor intensive. In addition, these techniques are inaccurate. Reverse transcription occurs at different efficiencies and kinetic rates depending on the nucleic acid sequences, artificially changing the concentration of specific nucleic acid sequences. Prokaryotic mRNA and some eukaryotic mRNA do not contain the poly A sequence or tail at the 3 prime end or the poly A tail may be degraded during purification, and therefore cannot be labeled or detected with the current techniques since there is no sequence to prime the reverse transcriptase step. The current techniques are thus restrictive to the types of samples which can be used for detection. Also, these methodologies involve labeled nucleotides. The incorporation of labeled nucleotides into unlabeled nucleic acids occurs at a lower efficiency and at a slower rate than natural nucleotides. Once more, labels may be incorporated with different efficiencies depending on the sequence. Therefore, the label density may differ between different sequences, artificially changing the measured amount of these nucleic acids. Thus, quantification is only relative. Labeled nucleic acids also exhibit different hybridization kinetics than natural nucleic acids, usually rendering them less specific. In addition, the present methods may require higher stringency hybridization conditions than unmodified nucleotides to achieve the same level of specificity. However, use of the higher stringency conditions to achieve acceptable specificity will lower the sensitivity of detection. Consequently, there is a need for an assay for detection and for quantitative analysis of biological molecules, including DNA, RNA, protein, and the like, that is accurate, both time and cost efficient, and capable of screening one or more sample biological molecules with great sensitivity and minimal non-specific binding.

Therefore, it may be useful to have a method to detect and measure the amount of one or more biological molecules, including, but not limited to RNA, DNA, or protein, that is easy to use, highly specific, accurate, and sensitive for screening biological molecules.

Accordingly, it is an object of the invention to provide an assay to detect the absence or presence, and quantify biological molecules, including, but not limited to RNA, DNA, or protein.

It is also an object of the present invention to provide a method of detecting an RNA:DNA hybrid comprising a specific target first biological molecule in a sample and a second biological probe.

It is an object of the present invention to provide a sensitive and quantitative assay having minimal false positives.

It is a further object of the present invention to provide an assay for massive parallel screening.

SUMMARY OF THE INVENTION

Disclosed is an assay for detecting and measuring a biological molecule of interest, including RNA, DNA, protein, and the like, in a sample by hybridizing the biomolecule to a complementary biomolecule probe forming double-stranded hybrids, followed by immunological detection of these double-stranded hybrids formed on a solid phase with an antibody or other entity which specifically recognizes RNA:DNA hybrids and is detectable. This method may be used to detect the presence of one or more specific biological molecules present in a variety of samples.

This invention provides for a method of simultaneously monitoring the amount (e.g. detecting and quantifying the amount) of a multiplicity of biological molecules.

The present invention relates to an assay for detecting RNA:DNA hybrids using detectably-labeled entities specific for recognizing RNA:DNA hybrids. Preferably, the entity is a detectably-labeled RNA:DNA hybrid-specific antibody or a fragment thereof. The antibody used for detecting the RNA:DNA hybrids may be monoclonal or polyclonal, and preferably polyclonal for detection of short biological molecule probes having a length of less than 30 bases.

The present invention also relates to an assay using the microarrays of the invention to determine physiological responses by gene expression, polymorphism mutation detection, SNP analysis, or the like. The method may be used to detect any and all genotypic variations, including insertion or deletion mutations.

Further, the present invention relates to an assay utilizing reverse transcriptase for extending short biological molecules, thereby enhancing detection of RNA:DNA hybrids. Preferably, the reverse transcriptase is thermostable and lacks RNAse H function.

The present invention further relates to a kit for the detection and quantification of biological molecules, wherein the kit may be used to screen samples for large numbers of targets described herein by the present invention.

BRIEF DESCRIPTION OF THE FIGURES

FIGS. 1A–D are a schematic representation of a preferred embodiment of the immunological antibody detection of RNA:DNA hybrids on microarrays. FIG. 1A shows hybridization of the RNA sample to the complementary DNA sequence that is attached to the microarray forming an RNA:DNA hybrid as depicted in FIG. 1B. Subsequently, antibodies, either monoclonal or polyclonal, bind the RNA:DNA hybrids, as seen in FIG. 1C. FIG. 1D illustrates the detection of fluorescent labels using a fluorescent laser scanner.

FIGS. 2A–D are a schematic representation of a second embodiment of the immunological detection of RNA:DNA hybrids on microarrays wherein the microarray comprises universal capture sequences. FIG. 2A shows the hybridization of the universal array with single-stranded DNA and sample RNA. Each hybrid formed on the microarray comprising a DNA:DNA region and an RNA:DNA region, as depicted in FIG. 2B. Antibodies detect and bind RNA:DNA hybrids in FIG. 2C. FIG. 2D illustrates one means of detection comprising fluorescent antibody labels using a fluorescent laser scanner.

FIGS. 3A–E are a schematic representation of a third embodiment of the immunological detection of RNA:DNA hybrids on microarrays wherein the microarray comprises expressed sequence tags (ESTs) for quantification of mRNA for which the full-length sequence is unknown. FIG. 3A shows the hybridization of sample RNA to the short ESTs bound to the microarray. The formation of RNA and short DNA hybrids is depicted in FIG. 3B. The DNA is extended to the full length of the RNA with the use of, for example, reverse transcriptase (RT), as demonstrated in FIG. 3C. FIGS. 3D and 3E illustrate antibody recognition of RNA:DNA hybrids and the detection of fluorescent antibody labels with laser scanner, respectively.

FIGS. 4A–D are a schematic representation of a fourth embodiment of the immunological detection of RNA:DNA hybrids on microarrays wherein the invention is directed to a 2-color detection method. FIG. 4A shows each DNA probe bound to the microarray containing a region of identical sequence and a region of variable sequence. The labeled DNA hybridizes with the common sequence and the RNA sample hybridizes with the variable sequence. RNA:DNA hybrids and DNA:labeled-DNA hybrids are formed, as demonstrated in FIG. 4B. Antibodies raised against RNA:DNA hybrids bind to the pertinent region; the microarray is scanned with fluorescent lasers of two different colors; and the signal is normalized as shown in FIGS. 4C–4D.

FIGS. 5A–D are a schematic representation of a fourth embodiment of the immunological detection of RNA:DNA hybrids on microarrays wherein the invention comprises a labeled degenerate n-mer DNA and sample RNA. FIG. 5A shows each DNA probe bound to the microarray simultaneously or sequentially hybridizing to the RNA sample and/or the labeled degenerate DNA. RNA:DNA hybrids and/or DNA:labeled-DNA hybrids are formed, as demonstrated in FIG. 5B. Antibodies raised against RNA:DNA hybrids bind to the pertinent region; the microarray is scanned with fluorescent lasers of two different colors; and the signal is normalized as shown in FIGS. 5C–5D.

DETAILED DESCRIPTION OF THE INVENTION

Figure 1A:
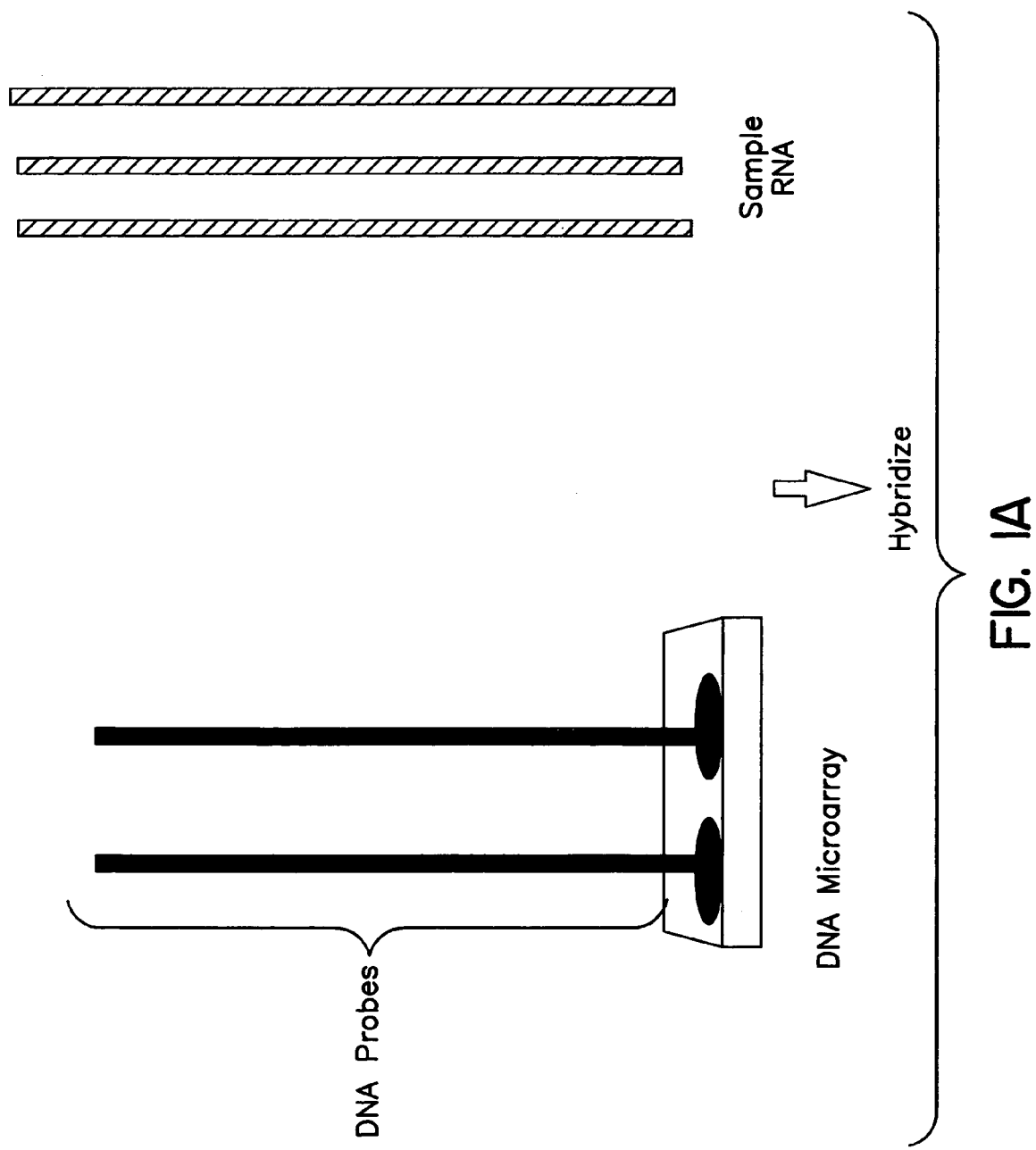
Figure 2A:
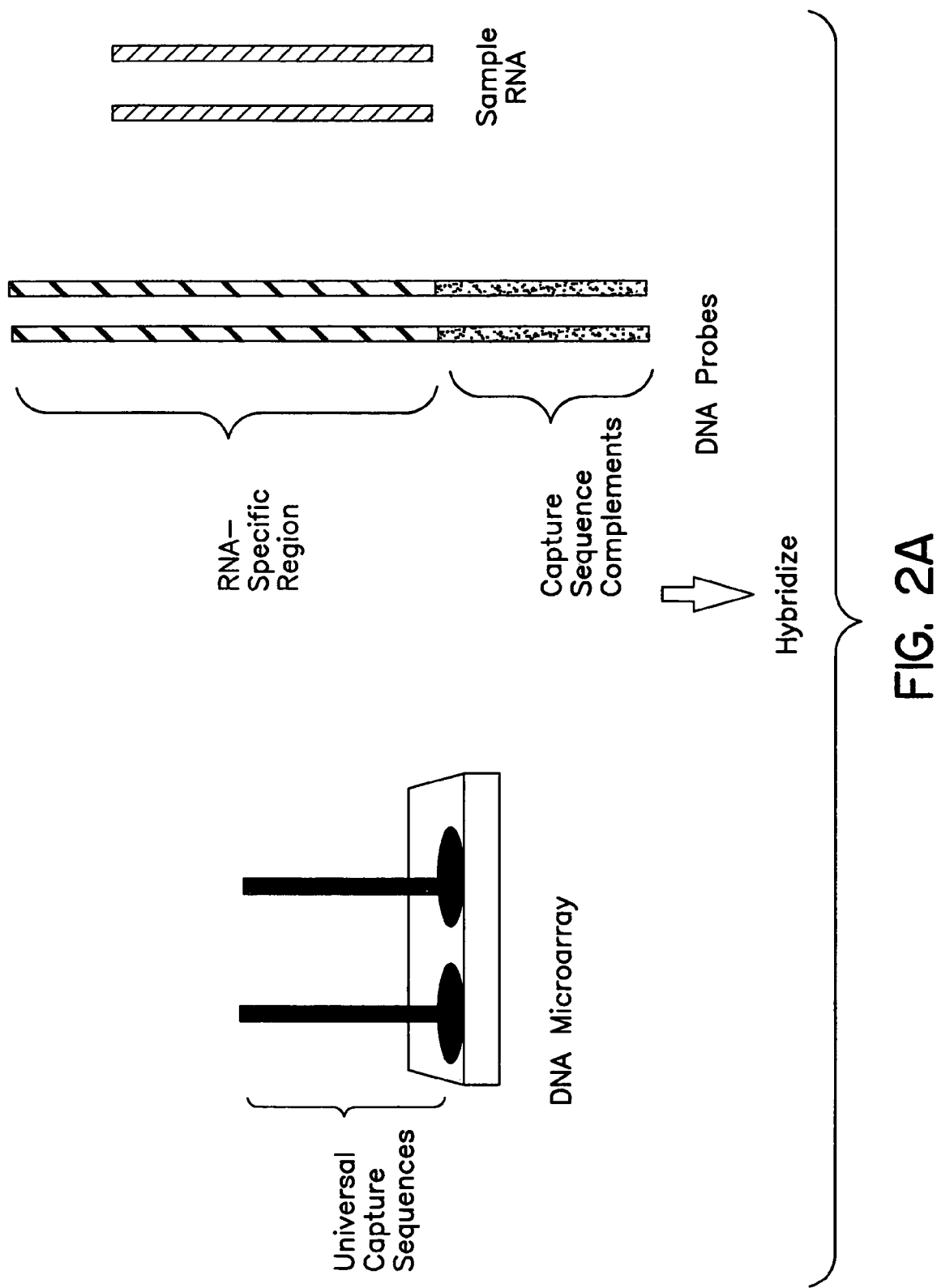
Figure 2C:
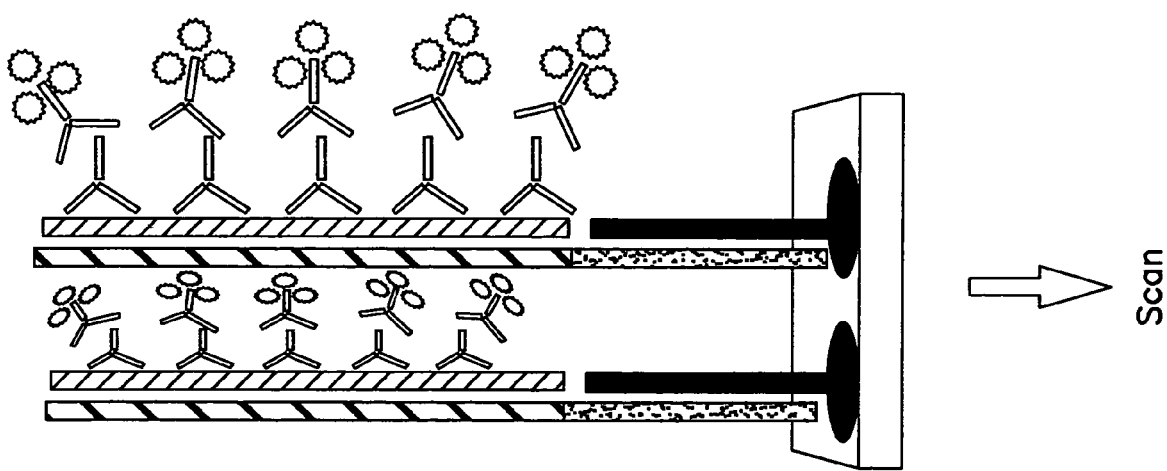
Figure 2D:
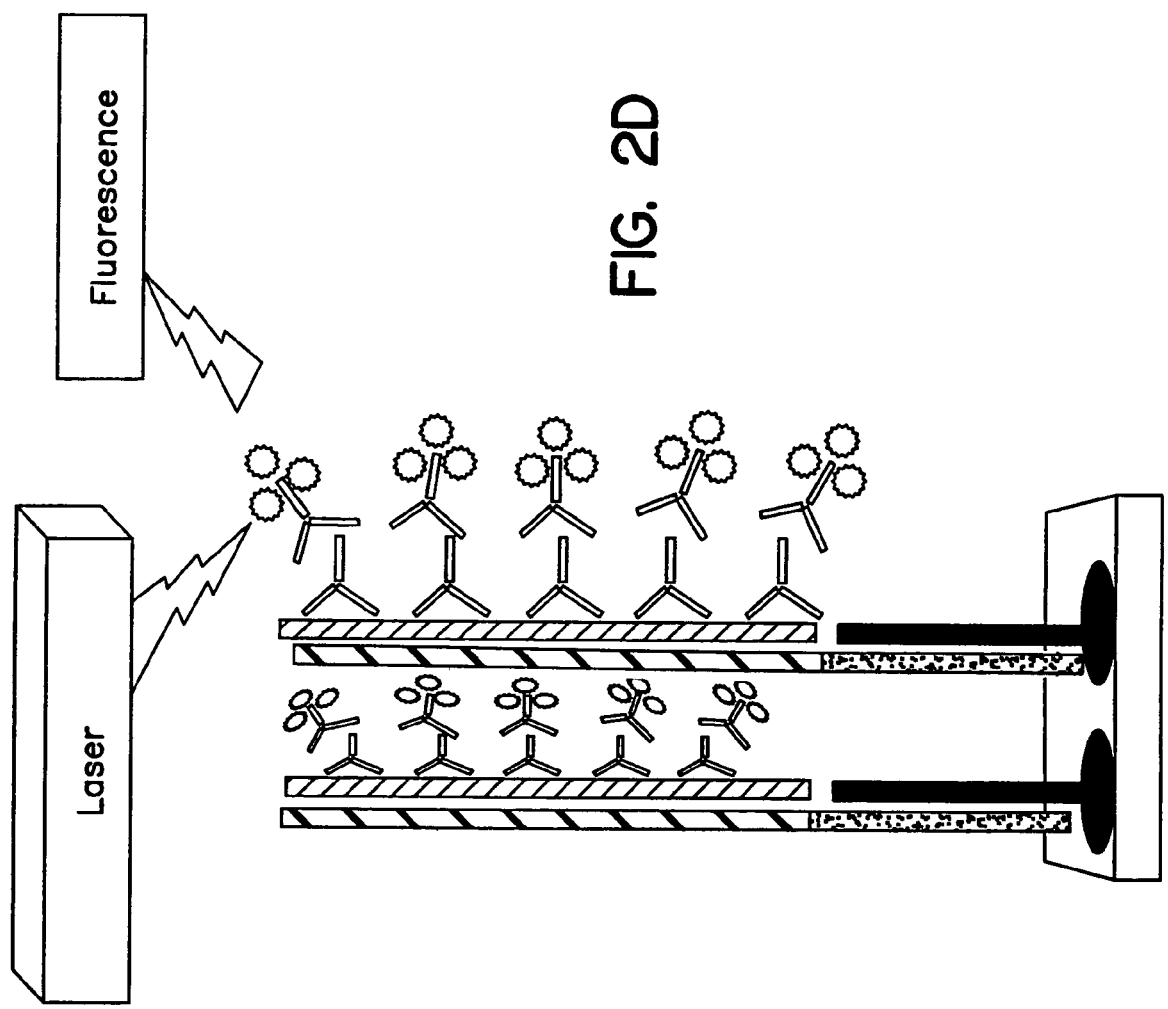
Figure 4A:
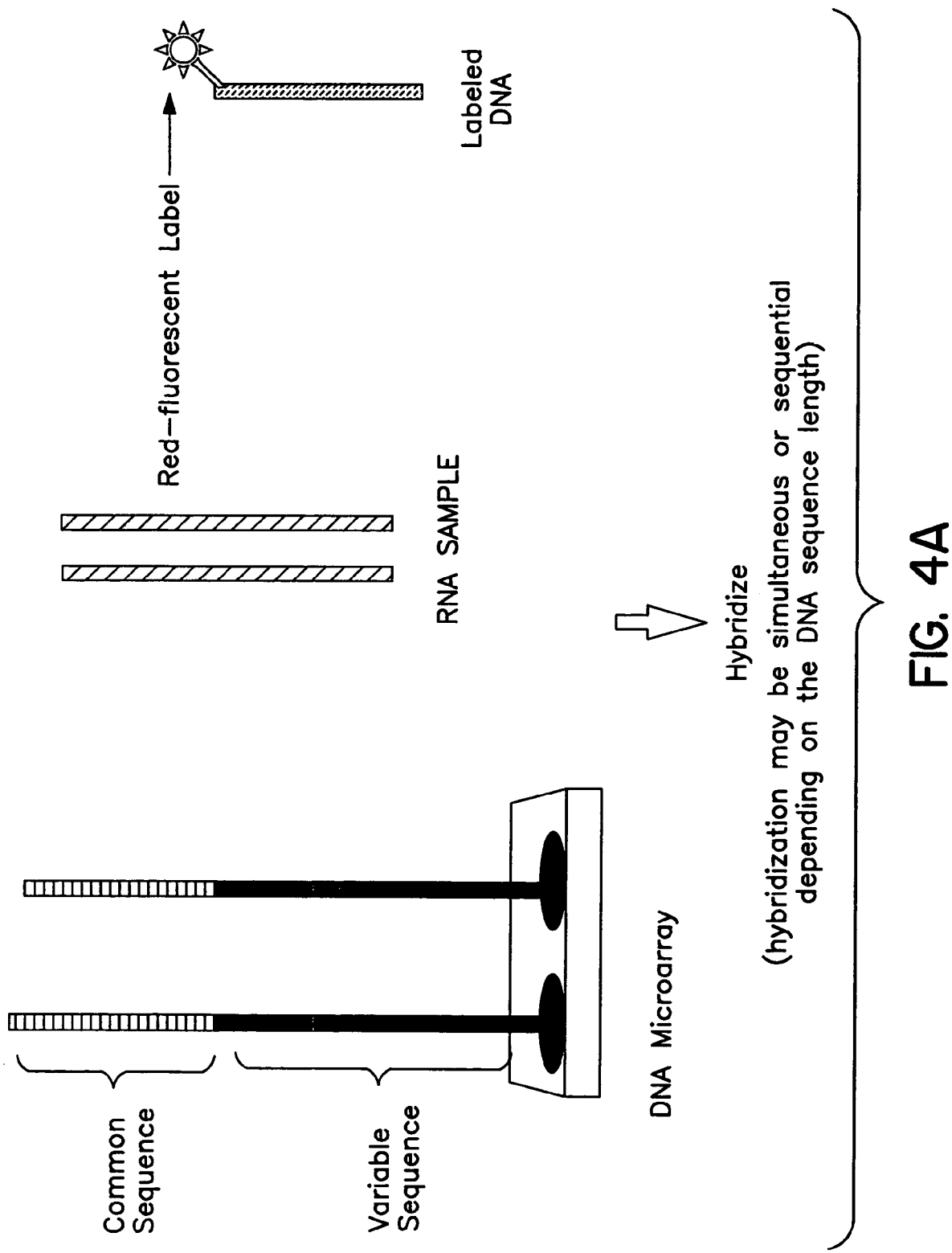
Figure 4D:
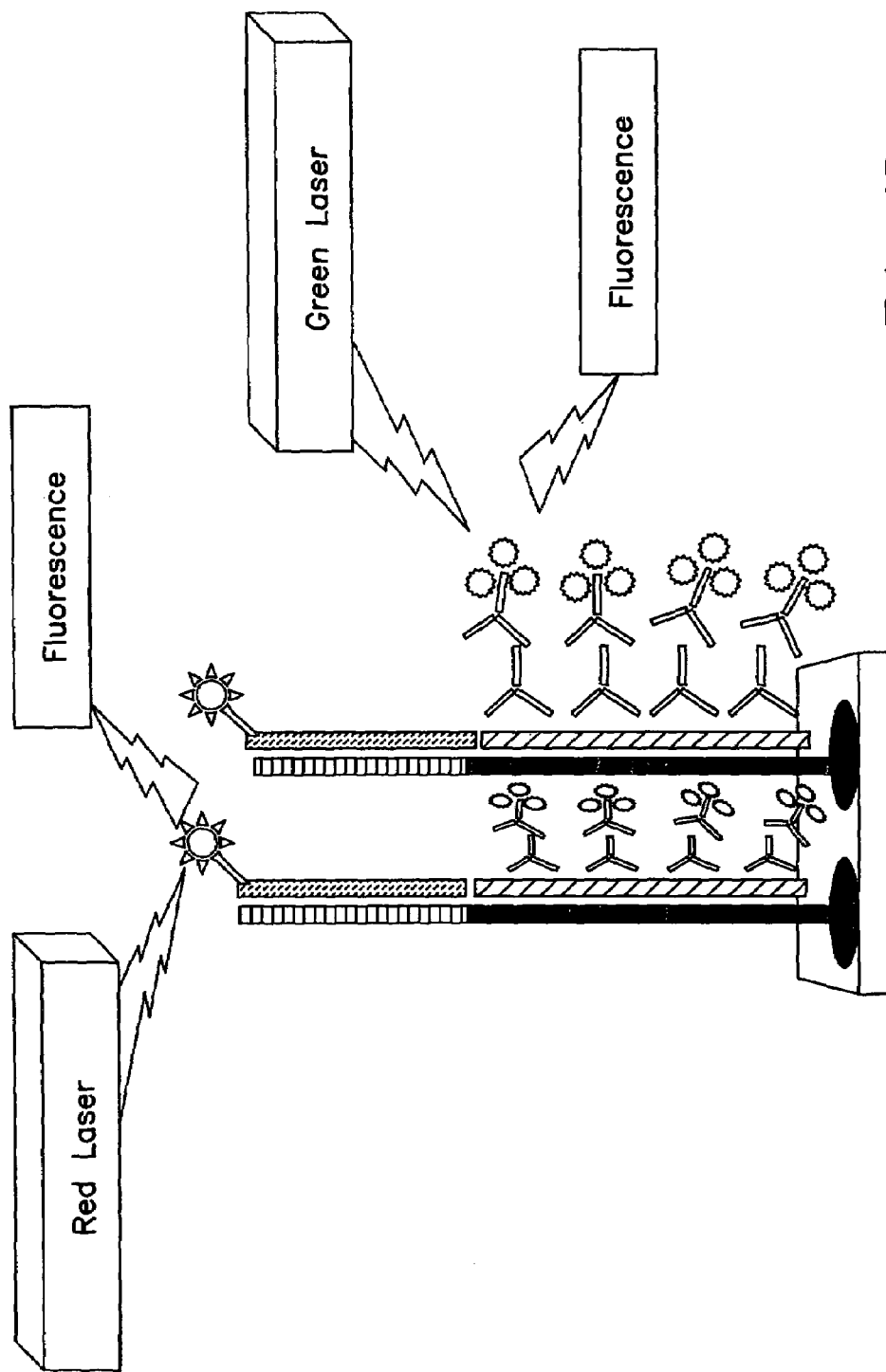
Figure 5A:
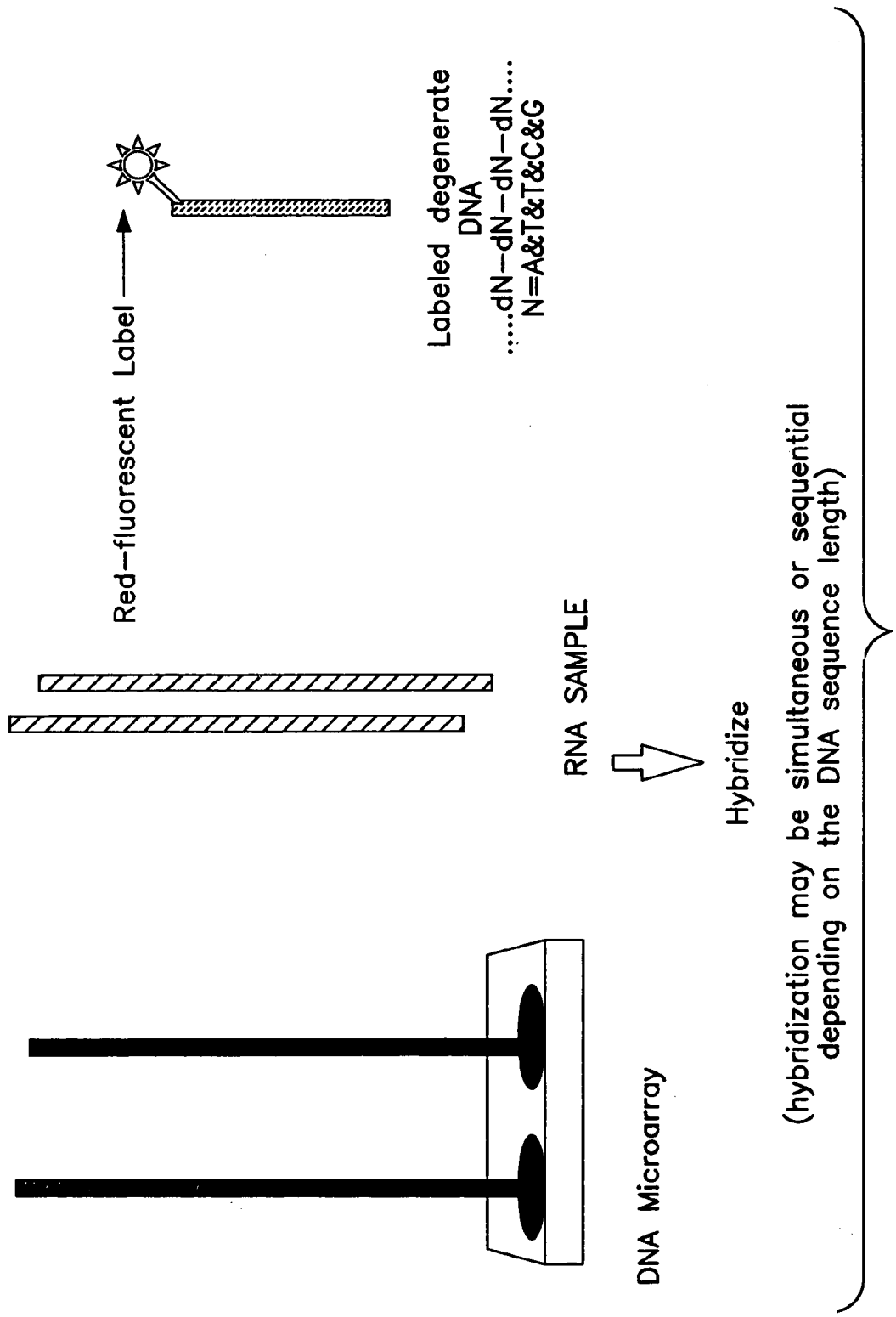
Figure 5D:
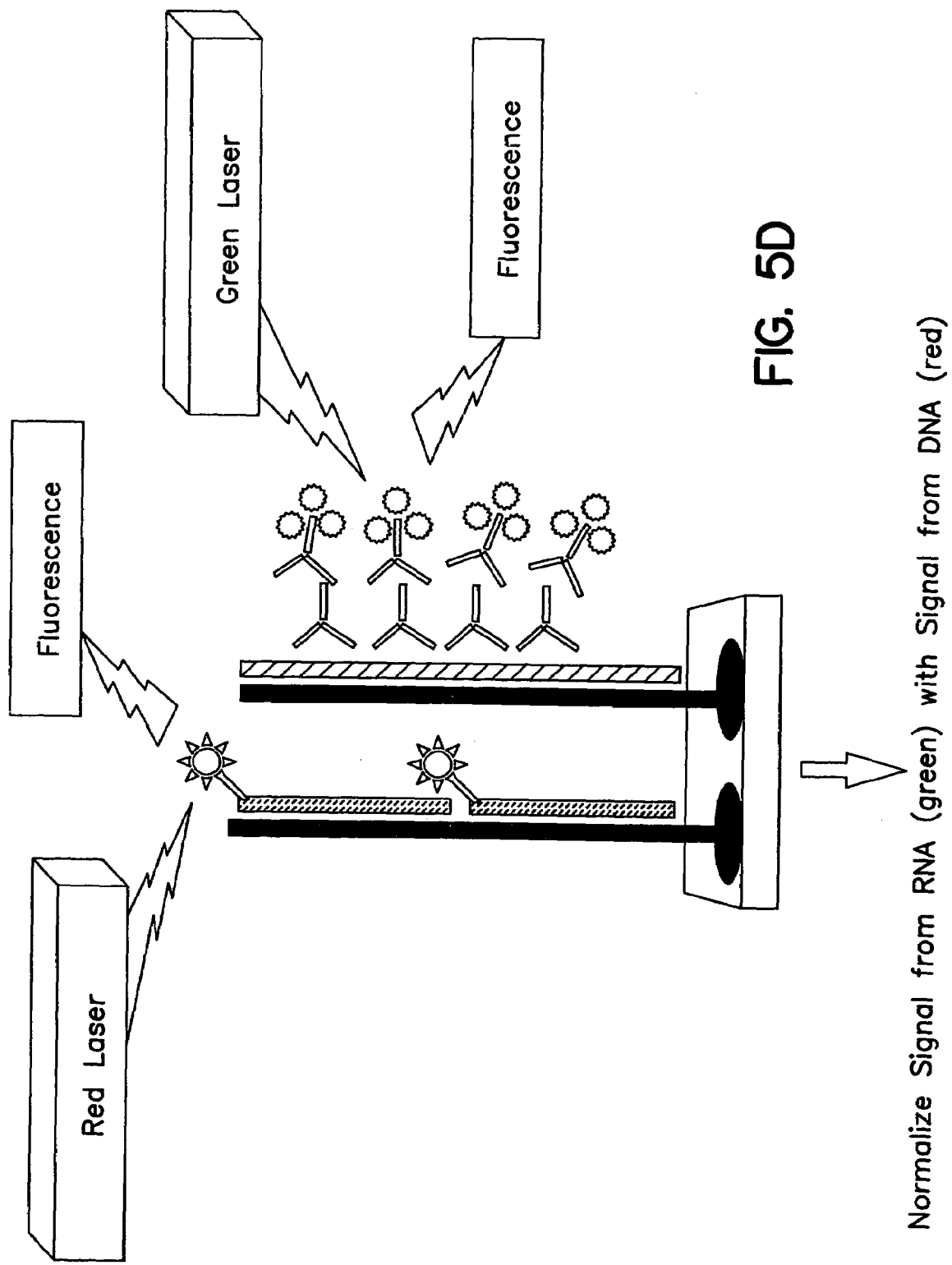

An assay and kit are provided for the detection and quantification of one or more target biological molecule in one or more samples. In general, a test sample comprising biological molecules, including, but not limited to RNA, DNA, protein, or the like, is collected and is either directly or indirectly, hybridized to a solid phase bound-nucleic acid probe specific for the target biomolecule. Non-hybridized nucleic acid sequences are removed, preferably by washing. Hybridization is then detected by a reaction with an RNA:DNA hybrid antibody that is labeled directly or indirectly with a detectable label, and/ or detected by a labeled nucleic acid sequence which is complementary to the bound nucleic acid probe sequence.

In one embodiment of the present invention, a specific nucleic acid of a sample is hybridized to a complementary nucleic acid probe, preferably using an oligonucleotide or other nucleic acid, which is spotted or synthesized to a solid phase, thereby forming a double-stranded RNA:DNA hybrid. Any entity which specifically recognizes RNA:DNA hybrids, preferably an antibody specific to an RNA:DNA hybrid, or fragment thereof, may be used for detection and measurement.

Also, the present invention utilizes short biological molecules, preferably primers or probes, immobilized to a solid phase. It may be desirable to extend the primers with a reverse transcriptase, preferably one lacking RNAse H function, enabling RNA:DNA hybrid-specific antibodies, RNA:DNA hybrid antibody fragments, or entities which specifically associate with RNA:DNA hybrids, to more efficiently bind and be detected.

A further embodiment of the present invention encompasses three biological molecules, all of which are preferably nucleic acids. A first sample biomolecule hybridizes to a complementary second biological molecule, preferably a probe, and either simultaneously or sequentially, hybridizes the second nucleic acid to a third nucleic acid, wherein one of the nucleic acids is immobilized to a solid phase, and the RNA:DNA hybrids which are formed, are detected by an entity specific for RNA:DNA hybrids.

In a further embodiment of the present invention, an immobilized biological molecule preferably comprising a protein, may bind to a sample biomolecule, preferably a nucleic acid, such that if the nucleic acid is an RNA:DNA hybrid, then it may be detected by an entity specific for RNA:DNA hybrids.

For example, DNA may bind a DNA binding site of the immobilized protein, wherein the DNA portion of the protein-DNA complex may be hybridized to RNA. In a similar manner, the immobilized protein may bind RNA, wherein the RNA portion of the protein-RNA complex may be hybridized to DNA. The resulting RNA:DNA hybrids may be detected by an entity specific for RNA:DNA hybrids, such as an RNA:DNA hybrid-specific antibody or fragment thereof.

The present invention provides significant advantages to the art in its use of microarrays. Since either crude or purified sample may be used, the invention has a simplified sample preparation process, allowing for a more accurate detection and measurement of biological molecules. Also, biological molecules need not be directly labeled for detection and measurement, thereby avoiding any interference attributed to the label. The present invention provides an extremely sensitive method for detecting and measuring biological molecules, since a very high labeling density may be achieved by utilizing an entity that binds to RNA:DNA hybrids. Such exquisite sensitivity reduces the amount of sample required for analysis. Unlike other methods, the current invention may measure prokaryotic mRNA and some eukaryotic mRNA that lacks a poly A tail or has been degraded after purification.

Another advantage of the present invention is that reverse transcription is not required, but it may be employed if desired for enhanced sensitivity. One of the most advantageous aspects of the present invention is direct quantification of biological molecules. Unlike the commonly used techniques which only relatively quantify RNA, e.g. 2-color competitive methods, the present invention utilizes a direct approach to interpret results and a simplified analysis of biological molecules. In addition, the present invention may simultaneously analyze a plurality of biological molecules due to its simplified sample process. Therefore the present invention allows much more straightforward interpretation and simplification of results.

In the present invention, a "probe" or a "nucleic acid probe", as used herein, is defined to be a collection of one or more nucleic acid or nucleic acid-like fragments whose hybridization to a second nucleic acid may be detected. The probe may be unlabeled or labeled as described below so that its binding to the second nucleic acid may be detected. The probe may be produced from a source of nucleic acids from one or more particular portions of the genome, which may be known or unknown, for example one or more clones, an isolated whole chromosome or chromosome fragment, a collection of polymerase chain reaction (PCR) amplification products, or a synthetic nucleic acid or PNA molecule. Alternatively, a probe may comprise a random, semi-random, or targeted sequence. The probe may be processed in some manner, for example, by blocking or removal of repetitive nucleic acids or enrichment with unique nucleic acids. Thus the word "probe" may be used herein to refer not only to the detectable nucleic acids, but to the detectable nucleic acids in the form in which they are applied to the target, for example, with the blocking nucleic acids. The blocking nucleic acid may also be referred to separately. What "probe" refers to specifically is clear from the context in which the word is used. A probe may also function as a primer in the context of its use as an initiation point for polymerization, i.e. for transcription or replication.

The probe may also be isolated nucleic acids immobilized on a solid surface. In some embodiments, the probe may be a member of a microarray of nucleic acids as described, for instance, in WO 96/17958. Techniques capable of producing high density microarrays may also be used for this purpose (see, e.g., Fodor et al. *Science* 767–773 (1991) and U.S. Pat.

No. 5,143,854 to Pirrung, M. C.). Probes may also be deposited as elements onto the reaction substrate for interrogating the target molecules, and may be either directly or indirectly labeled.

The disclosed assay of the present invention may be used to detect and quantify any biological molecule, or combination of biological molecules in a sample, wherein the term "biological molecule" and "biomolecule" used interchangeably, as defined herein, refers to nucleic acids, amino acids, analogues, peptides, antibodies, and the like. "Nucleic acid" refers to deoxyribonucleotides or ribonucleotides and polymers thereof, from any source, including, but not limited to synthetic or derived from bacteria, yeast, viruses, and the cells or tissues of higher organisms such as plants or animals, and unless otherwise limited, may encompass known analogs of natural nucleotides that may function in a similar manner as naturally occurring nucleotides. Peptide nucleic acids (PNAs) are also encompassed within the scope of the term nucleic acid.

A "nucleic acid" is further defined herein as a single- or double-stranded nucleic acid ranging in length from 2 to about 10,000 bases. As also used herein, the term "nucleic acid" refers to oligonucleotides, cDNA, mRNA, amplicons, plasmids, and the like. An "oligonucleotide" is one preferred nucleic acid probe comprising of at least 6 to about 60 nucleotides, preferably about 15 to 30 nucleotides, and more preferably about 20 to 25 nucleotides, which may be used in PCR amplification or a hybridization assay, or a microarray. As used herein, oligonucleotide is substantially equivalent to the terms "amplimers" and "oligomers", as commonly defined in the art, and may be used as "primers" and "probes" as described herein.

Also, unless otherwise limited, the term encompasses nucleic acids containing known analogues of natural nucleotides which have similar binding properties as the reference nucleic acid and are metabolized in a manner similar to naturally occurring nucleotides. In addition, a particular nucleic acid sequence also implicitly encompasses conservatively modified variants thereof (e.g. degenerate codon substitutions) and complementary sequences as well as the sequence explicitly indicated.

Nucleic acid sequences for detection, referred to herein as nucleic acid molecules of interest, or target nucleic acid molecules, are selected based on the needs and purpose of the detection. In general, a nucleic acid molecule of interest may be chosen based on known criteria for selecting a nucleic acid sequence for detection. For example, a particular nucleic acid molecule may be associated with a pathogen, a disease state, or a predisposition to a disease, and detection of such a nucleic acid molecule may have a diagnostic value. For example, mRNA specific to tumor cells or normal cells may be detected. In addition, the disclosed method also allows the detection of a biological molecules comprising, but not limited to, protein, peptides, primers, and DNA or RNA molecules, generated by other biochemical or chemical methods such as those generated by CAR, NASBA, etc. The detection of nucleic acids also includes that of mutations, deletions, insertions of single nucleotide polymorphisms, and other polymorphisms.

A "sample" or "target sample" as used interchangeably herein, is defined in its broadest sense and includes both biological material and synthetic material of biological molecules, including, but not limited to nucleic acids, amino acids, proteins, peptides, and the like, and refers to a sample comprising total genomic DNA, total RNA, genomic DNA or mRNA from, for example chromosomes, or selected sequences (e.g. particular promoters, genes, amplification or restriction fragments, cDNA, etc.) within particular amplicons or deletions. An embodiment of the present invention is to detect either the presence or absence of the target nucleic acid sample and to measure the amount of the sample that is to be quantified. The term "target nucleic acid" may refer to the specific subsequence of a larger nucleic acid to which the probe is directed to or to the overall sequence (e.g., gene or mRNA) whose level is desired to detect, quantify, and determine the presence or absence. The difference in usage will be apparent from the context.

The biomolecule sample may be extracted from particular cells or tissues. The tissue sample from which the biomolecule sample is prepared is typically taken from a patient suspected of having the disease associated with the amplification or deletion being detected. In some cases, the biological molecules, for example, nucleic acids, may be amplified using standard techniques such as PCR, prior to the hybridization. The particular usage of the term "nucleic acid sample" will be readily apparent to one of skill in the art from the context in which the term is used. For instance, the nucleic acid sample may be a tissue extract or cell lysate sample prepared by methods known in the art. The sample is prepared such that biological molecules of interest are released from cells and are available for hybridization.

Alternatively, a sample for the disclosed method of the invention may be from any source containing or suspected of containing nucleic acid. The source of nucleic acid may be in purified or non-purified form. Preferred types of samples, or sources of samples, that are suitable for use in the disclosed method are those samples already known or identified as samples suitable for use in other methods of nucleic acid detection. Many such samples are known. For example, the sample may be from an agricultural or food product, or may be a human or veterinary clinical specimen. Samples may be a biological fluid such as plasma, serum, blood, urine, sputum, cell lysate, or the like. The sample may contain bacteria, yeast, viruses and the cells or tissues of higher organisms such as plants or animals, suspected of harboring a biological molecule of interest. Methods for the extraction and/or purification of nucleic acids, for example, RNA have been described by Maniatis et al., Molecular Cloning: A Laboratory Manual (New York, Cold Spring Harbor Laboratory, 1982).

Since samples may also be in a crude or unpurified state, the sample preparation or processing is simplified. By using samples found in a more natural state, accurate expression detection and quantification is achieved. In addition, unlike other techniques which require the presence of a poly A sequence for priming the reverse transcriptase step in order to label and detect sample, the present invention may be used to measure prokaryotic mRNA and eukaryotic mRNA that does not have a poly A tail at the 3 prime end.

Target biological molecules of interest for use in the disclosed method may come from various sources, both natural and synthetic. For example, various types of RNA include messenger RNA, ribosomal RNA, nucleolar RNA, transfer RNA, viral RNA and heterogeneous nuclear RNA, total genomic DNA, cDNA, proteins, peptides, or the like. In addition, whole naturally occurring entities or fragments thereof may be used.

Solid phases or solid supports include, but are not limited to, those made of plastics, resins, polysaccharides, silica or silica-based materials, functionalized glass, modified silicon, carbon, metals, inorganic glasses, membranes, nylon, natural fibers such as silk, wool and cotton, and polymers. Solid phases or solid supports may be porous or non-porous. In some embodiments, the material comprising the solid support has reactive groups such as carboxy, amino, hydroxy, etc., which are used for covalent or non-covalent attachment of the probes. Suitable polymers may include, but are not limited to, polystyrene, polyethylene glycol tetraphthalate, polyvinyl acetate, polyvinyl chloride, polyvinyl pyrrolidone, polyacrylonitrile, polymethyl methacrylate, polytetrafluoroethylene, butyl rubber, styrenebutadiene rubber, natural rubber, polyethylene, polypropylene, (poly)tetrafluoroethylene, (poly)vinylidenefluoride, polycarbonate and polymethylpentene. Preferred polymers include those outlined in U.S. Pat. No. 5,427,779 to Elsner, H. et al., hereby expressly incorporated by reference. Solid phases and solid supports include, and are not limited to, any solid material to which the probes, primers, oligonucleotides, proteins, peptides, or the like, may be coupled or adhered. Solid phases and solid supports may have any useful form including thin films or membranes, beads, bottles, microwell plates, dishes, slides, fibers, woven fibers, shaped polymers, particles, chips and microparticles. Preferred substrate forms for a solid phase are microtiter dishes, silicon chips, glass slides, and tagged beads.

For general application, where a molecule is to be covalently bonded to the solid substrate surface, the surface may be activated using a variety of functionalities for reaction, depending on the nature of the bound component and the nature of the surface of the solid substrate. Thus the surface of the solid substrate, if required, may be modified by the introduction of functionalities which may then react with the bound component.

"Microarrays" comprise a plurality of different biological molecules including cDNA, amplicons, plasmids, proteins, peptides, and the like, where a plurality encompasses at least two different biological molecules, where the biomolecules are deposited, synthesized, or immobilized in a pre-determined spatial order to a solid phase in an ordered or arranged matrix or structure allowing the biomolecules to be made available as probes in a high-throughput, parallel manner.

In theory, there need be only one component, but in a preferred embodiment there will be at least 10, more usually at least 20, frequently at least 50, desirably 100 or more, and even 1,000 or more, but usually not more than about $10^4$, more usually not more than about 100,000, with from about 10 to 10,000 immobilized to a solid phase or solid support being preferred. While theoretically the number of different components may exceed $10^5$, due to the ability to specifically have a small amount or volume at a specified finite site, for the most part there is no need to exceed 100,000 and such large numbers of different components do add some complexity to the preparation of the microarray. As the number of components immobilized to a solid phase will usually not exceed $10^5$, the number of individual addressable sites may be substantially larger, depending on the nature of the bound component, the source of the signal, the nature of the signal which is detected, the sensitivity with which the signal may be detected, the nature of the bound microarray, such as the size of the microarray, the manner in which the microarray is produced, and the like. Therefore, microarrays are preferably used for "massive parallel screening", described herein as the simultaneous screening of at least about 10, preferably about 1,000, and more preferably about 10,000, different biological molecule hybridizations.

One preferred form of a microarray comprises a spotted array to which 1–10, 10–100, or most preferably more than 100 separate nucleic acids, preferably oligonucleotides, primers, or the like, may be deposited, may be spotted or synthesized as an ordered array of small dots or elements, as described herein. These nucleic acids, deposited, spotted, or synthesized on a solid phase, are referred to herein as "elements". Typically, an element will be less than about 1 mm in diameter. Generally, element sizes are from 1 μm to about 5 mm, preferably between about 1 μm and about 1 mm, and more preferably, the diameter of a sample detection spot or element may range from about 1 to about 150 micrometers. Microarrays may be spotted at varying densities. Low-density spotting ranges from 1 to about 200 spots per $cm^2$, medium-density spotting ranges from about 200 to about 400 spots per $cm^2$, while high-density spotting ranges from about 400 to about 10,000 spots per $cm^2$. Nucleic acid primers for use in the disclosed method may be synthesized using established oligonucleotide synthesis methods. Such methods range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1 Plus DNA synthesizer (for example, Model 8700 automated synthesizer of Milligen-Biosearch, Burlington, Mass. or ABI Model 380B). Synthetic methods useful for making oligonucleotides are also described by Ikuta et al. (*Ann. Rev. Biochem.* 53:323–356 (1984), (phosphotriester and phosphite-triester methods)), and Narang et al. (*Methods Enzymol.*, 65:610–620 (1980), (phosphotriester method)).

Another form of microarray is a three dimensional array, examples of which include an array of color-coded beads (Luminex; Austin, Tex.) and an array of radiofrequency-tagged beads (PharmaSeq; Monmouth Junction, N.J.). A three dimensional microarray, as used herein, is any solid phase having three dimensions, wherein each microarray comprises a plurality of different biological molecules, preferably nucleic acid primers, attached to the surface. Thus, the location of each primer on the solid phase microarray enables the identification of each nucleic acid primer sequence. Manipulations of the disclosed assay may be utilized. For example, a three-dimensional microarray comprising of a plurality of nucleic acid primers may be mixed with target nucleic acids of interest. When the primers are short, it may be desirable to extend these molecules with polymerases, such as for example reverse transcriptase, so as to incorporate the binding capacity of the RNA:DNA hybrid-specific entity, as described herein, including antibodies and fragments thereof. By capturing the antibodies on a solid phase, the primers of the solid phase microarray on which RNA:DNA hybrids have formed may be separated from the primers where no hybrid has formed. The entities specific for RNA:DNA hybrids may then be detected and the identities of the primers determined. Many other assay schemes may be used for the disclosed method.

The microarray has emerged as a preferred format for the miniaturization of assays that detect and measure RNA, DNA, proteins, and the like, for application towards, for example, gene expression, mutation and polymorphism analysis, SNPs, detection of genetic variations, etc. Microarrays allow the level of tens to several thousands of genes or genetic variations (for example SNPs) to be measured from a single sample on a single device. A weakness of the traditional microarray methods is that the biological molecule, preferably nucleic acid (either RNA or DNA) to be measured, must first be labeled, often through conversion of one type of nucleic acid to another, for example RNA to labeled DNA, so that it may be detected and measured.

The present invention preferably utilizes a "nucleic acid microarray", which as defined herein, comprises a plurality of nucleic acid sequences, including, but not limited to, DNA, RNA, amplicons, plasmids, and the like, immobilized to a solid support to which complementary target nucleic acids are hybridized. The nucleic acids of the microarray may, for example, contain sequence from specific genes or clones, probes, primers, or oligonucleotides, bound to a porous or non-porous solid phase or solid support. Nucleic acids of various dimensions may be used in the microarrays of the invention.

The nucleic acids may be coupled to the solid support or substrate. Such a microarray is a solid support to which multiple different nucleic acids have been coupled or adhered in an array, grid, or other organized pattern. "Nucleic acid microarrays" preferably comprise arrays of nucleic acid sequence strands on silicon chips, glass slides, or other solid support, and are in widespread use for detection and measurement of gene expression, mutation and polymorphism analysis, etc. Several methods are available for preparing nucleic acid microarrays. Strands of nucleic acid sequences may be non-covalently or covalently bound to a solid substrate through passive or chemical coupling methods. Other approaches utilize synthetic methods to build the nucleic acid molecules directly on the surface of the substrate. A simpler, but more limited approach, is to prepare labeled nucleic acid sequences and then bind the labeled nucleic acid sequences to a substrate that has been coated with a binding partner.

Alternatively, elements of proteins and/or peptides may be coupled to the solid support or substrate in an organized pattern. These immobilized protein elements may be bound by nucleic acids, proteins, peptides, and/or nucleic acid hybrids. Detection is achieved using entities specific for RNA:DNA hybrids, such as antibodies or fragments thereof. If the protein or peptide binds RNA:DNA hybrids, then the RNA:DNA hybrid portion of the protein-hybrid complex may be detected using an entity specific for RNA:DNA hybrids. If the protein binds DNA, then the DNA portion of the protein-DNA complex can be hybridized to RNA resulting in the formation of an RNA:DNA hybrid. If the protein binds RNA, then the RNA portion of the protein-RNA complex may be hybridized to DNA, resulting in the formation of an RNA:DNA hybrid. The RNA:DNA hybrids may be detected using an entity specific for RNA:DNA hybrids, such as RNA:DNA hybrid-specific antibodies, or their fragments thereof.

A "hybrid" is a double-stranded nucleic acid comprising RNA or DNA. The duplex may be DNA:DNA, RNA:RNA, or RNA:DNA, or may comprise artificial nucleotides. An RNA homoduplex is a base-paired double-stranded RNA. An RNA:DNA heteroduplex comprises an RNA strand and a strand comprising DNA nucleotide monomers. All or a region of the duplex may be double-stranded. Typically, at least 10 bases of the duplex will be double-stranded. The phrases "to specifically hybridize" or "specific hybridization" or "selectively hybridize to", or the like, refer to the binding, duplexing, or hybridizing of a nucleic acid molecule preferentially to a particular nucleotide sequence under stringent conditions when that sequence is present in a complex mixture (e.g., total cellular) DNA or RNA.

Nucleic acid probes immobilized on a solid substrate allow formation of RNA:DNA hybrids localized on the substrate. Such localization provides a convenient means of washing away reaction components that might interfere with subsequent detection steps, and a convenient way of assaying for multiple different target nucleic acid sequences simultaneously. RNA:DNA hybrids may be independently formed at each site where a different primer is adhered. For immobilization of probes to form a solid phase microarray of biological molecules, the methods described herein may be used.

An "entity", as defined herein, refers to any molecule which specifically recognizes RNA:DNA hybrids. Examples of entities that may recognize RNA:DNA hybrids may include, but are not limited to, chimeric antibodies, and natural or genetically engineered proteins or nucleic acids that specifically bind to RNA:DNA hybrids.

One preferred embodiment of entity is "antibody". As used herein, antibody is intended to be used in the broadest sense and to include whole, intact antibodies, antibody fragments, recombinant antibodies, chimeric antibodies, polyfunctional antibody aggregates, or in general any antibody-derived substance that comprises at least one antibody combining site having the characteristics described herein or other entities. Preferably, in the present invention, these entities, specifically detect and bind RNA:DNA hybrids. Antibodies of any of the known classes and subclasses of immunoglobulins are contemplated, for example, IgG, IgM, and so forth, as well as active fragments such as the IgG fragments conventionally known as Fab, F(ab'), and F(ab')2. Antibodies may comprise monoclonal antibodies (including agonist, antagonist, and neutralizing antibodies) which bind to a specific epitope and polyclonal antibodies having polyepitopic specificity, or other entities.

Any antibodies or entities specific for double-stranded RNA:DNA hybrids may be used to directly detect the hybrid of the invention. In the present invention, polyclonal antibodies are preferred in the embodiment which utilizes them for detecting short nucleic acid sequences, preferably those less than 30 bases in length.

The antibodies used to detect RNA:DNA hybrids may be either monoclonal or polyclonal antibodies. It may also be advantageous to use a mixture of monoclonal and polyclonal antibodies. Furthermore, the invention includes the use of customized polyclonal or monoclonal antibodies that may be produced with specific binding properties. For instance, monoclonal or polyclonal antibodies that specifically bind to very short (less than 20 base pairs) RNA:DNA hybrids may be produced and may find use in detecting very short RNA:DNA hybrids. In addition, monoclonal or polyclonal antibodies may be produced that are either more or less sensitive to mismatches within the RNA:DNA hybrid. Antibodies which are more sensitive to mismatches within the RNA:DNA hybrid will find extra utility in the detection of genetic variation while antibodies which are less sensitive to mismatches with the RNA:DNA hybrid will find use in the detection and quantification of specific classes of nucleic acids. Other antibodies may also be used that specifically detect nucleic acid triplexes (DNA:RNA:DNA or RNA:DNA:RNA) or DNA:PNA or RNA:PNA hybrids, wherein PNA is defined herein as peptide nucleic acid.

Polyclonal antibodies directed against the RNA:DNA hybrids are prepared by injecting a suitable laboratory animal with an effective amount of the peptides or antigenic component, collecting serum from the animal, and isolating specific sera by any of the known immunoadsorbent techniques. Animals which may readily be used for producing polyclonal RNA:DNA hybrid antibodies include chickens, mice, rabbits, rats, goats, horses, and the like. In a preferred embodiment of the present assay, a polyclonal RNA:DNA hybrid antibody is derived from goats immunized with an RNA:DNA hybrid. Hybrid-specific antibody is purified from the goat serum by affinity purification against RNA:DNA hybrid immobilized on a solid support.

Monoclonal antibodies, prepared by standard techniques, may be used in place of the polyclonal antibodies. A variety of techniques may be used to obtain suitable antibodies specific for RNA:DNA hybrids. (For example, U.S. Pat. No. 4,833, 084 to Carrico, U.S. Pat. No. 4,732,847 to Stuart et al. and Stuart et al., *Proc. Natl. Acad. Sci. USA* 78:3751 (1981)). A monoclonal antibody specific for RNA:DNA hybrids, secreted by hybridoma HB 8730, is disclosed in U.S. Pat. No. 4,833,084 to Carrico. Preferably, in accordance with the present invention, monoclonal antibodies are used for the detection of nucleic acids greater than 30 bases in length.

The isolation of anti-RNA:DNA hybridomas has improved the development of assays for genetic mutations linked to specific defects and the detection of bacterial and viral infections. However, assays utilizing these RNA:DNA hybrid-specific monoclonal antibodies often suffer from a high level of non-specific binding causing false positive results. Boguslawski et al., *J. Immunol. Methods* 89:123–130 (1986) developed a hybridization assay using anti-hybrid coated polystyrene beads isolated on filter paper in an attempt to reduce non-specific binding and avoid complicated washing procedures.

The preferred antibody for RNA:DNA hybrids is prepared by the method of Kitawaga, Y. and Stollar, B. D., *Mol. Immunology* 19:413–420 (1982) or according to the method set forth in U.S. Pat. No. 4,732,847, issued Mar. 22, 1988 to Stuart et al., both of which are incorporated herein by reference.

The identification of the presence of the hybrids may be achieved by employing either polyclonal or monoclonal antibodies or other entities specific for the RNA:DNA hybrid complex. Detection may be achieved by labeling either the antibody specific for the hybrid RNA:DNA complex, or by employing labeled antibodies which bind to the anticomplex. For example, where the antibody is derived from a mouse, antibodies to mouse antibodies, for example rabbit anti (-mouse IgG), may be labeled so as to bind to any anticomplex bound to the complex bound to the solid support.

A wide variety of labels have been used in other environments which may be applicable here. One of the more common labels is radionuclides, which may be used with autoradiography to visualize the areas of binding. Another label is a fluorescer such as fluorescein, mercocyanine, or rhodamine which by irradiation with light of excitation, the presence of fluorescence may be monitored. Alternatively, an enzyme may be used which results in a product which may be detected and localized in the area of the enzyme. A large number of dyes or metals capable of reduction may be employed to provide detection. Common enzymes include horseradish peroxidase, glucose oxidase, galactosidase, alkaline phosphatase, or the like. The particular label or manner in which the detectable signal is observed is not critical to this invention. By employing antibodies to the anticomplex, the number of labels associated with a particular binding of the anticomplex to the complex may be greatly amplified.

To facilitate detection of resulting binding of the antibody, or the other entity specific for double-stranded hybrids, to the hybrid, the antibody will normally be labeled with a detectable chemical group. Examples of detectable chemical groups that may serve as labels are enzymatically active groups, such as coenzymes, enzyme substrates, enzyme inhibitors, and enzymes themselves, fluorescers, chromophores, luminescers, specifically bindable ligands such as biotin or haptens which are detectable by binding of labeled avidin or labeled hapten antibodies, and radioisotopes.

In order for complete hybridization to occur, the optimal conditions are necessary for forming double-stranded hybrids. The term "stringent conditions" refers to conditions under which a probe will hybridize preferentially to a complementary sequence, and to a lesser extent to, or not at all to, other sequences. Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules. A "stringent hybridization" and "stringent hybridization wash conditions" in the context of nucleic acid hybridization experiments, such as, for example, Southern and Northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes* part 1 chapter 2. "Overview of principles of hybridization and the strategy of nucleic acid probe assays", Elsevier, N.Y.

"Bind(s) substantially" refers to complementary hybridization between a probe nucleic acid and a target nucleic acid and embraces minor mismatches that may be accommodated by reducing the stringency of the hybridization media to achieve the desired detection of the target polynucleotide sequence hybridized to the bound oligonucleotide sequence, which includes cDNA, amplicons, plasmids, and the like.

Hybridization of the probe nucleic acid to the nucleic acid molecule of interest may be carried out under any suitable conditions, and preferably under conditions which favor hybridization and form double-stranded hybrids. See for example, Sambrook et al., *Molecular Cloning: A Laboratory Manual,* 2nd Edition (Cold Spring Harbor Laboratory Press, Cold Spring Harbor, N.Y., 1989).

For example, in one embodiment of the present invention, a primer is needed to begin reverse transcription. A "primer" is defined herein, as a nucleic acid molecule that may anneal to a DNA or RNA template molecule and serves as the initiation point for nucleic acid synthesis. A custom primer is generally a synthetic oligonucleotide, including cDNA, amplicons, plasmids, and the like, but naturally occurring nucleotides act as primers as well, both in vitro and in vivo. In vitro uses of primers include, for example, cDNA synthesis, Sanger dideoxy sequencing, and PCR.

This particular embodiment requires a nucleic acid "template" of interest in order to identify the target nucleic acid(s) of interest once the target nucleic acid sample(s) are obtained. Wherein, "nucleic acid template" or "template" as used interchangeably herein, is defined as a polynucleotide sequence from which information is read to direct synthesis of another macromolecule. For example, this may refer to a DNA strand being copied during DNA synthesis or transcription of RNA, to an RNA strand being copied during reverse translation.

A primer of the disclosed method may be an oligonucleotide, cDNA, amplicons, plasmids, and the like, either RNA or DNA, having sequence complementary to a region on a nucleic acid molecule of interest. As used herein, the complementary sequence of the primer is referred to as the "complementary portion". As used herein, the region on the target nucleic acid molecule of interest complementary to the primer is referred to as the "primer complement region". The primer complement region of a target nucleic acid molecule of interest may be any region of the target molecule of interest. For the embodiment of the present assay which utilizes reverse transcriptase, a preferred mode comprises the primer complement region of a target nucleic acid molecule be at some distance from the 5 prime end of the template nucleic acid molecule. This provides a longer region of nucleic acid template between the site of primer hybridization and the end of the template nucleic acid molecule, thereby amplifying the amount of RNA:DNA hybrid to be detected.

In general, the primer complement region of a nucleic acid molecule of interest is chosen based on known criteria for selecting a nucleic acid sequence for detection. For example, to detect a particular nucleic acid molecule from among other nucleic acid molecules, it is preferred that the primer complement region is characteristic of, or unique to, the target nucleic acid molecule of interest. If it is desired that any of a class of RNA molecules be detected, it is preferred that the primer complement region is chosen to have a sequence that is the same or substantially the same in all of the target nucleic acid molecules of interest. Once a primer complement region is selected, the sequence of the primer is designed or chosen to be complementary to the chosen primer complement region of the molecule of interest. Any nucleic acid molecule for which a sequence is known or for which a sequence may be derived may be detected using the disclosed method.

In the method of the invention the complementary portion of a primer has a length that supports specific and stable hybridization between the primer and the primer complement region. Generally a primer of the present invention comprises 10 to 100 nucleotides, but is preferably 15 to 30 nucleotides.

The ability to characterize an individual by its genome is due to the inherent variability of genetic information. Although DNA sequences which code for necessary proteins are well conserved across a species, there are regions of DNA which are non-coding or code for portions of proteins which do not have critical functions and therefore, absolute conservation of nucleic acid sequence is not strongly selected for. These variable regions are identified by genetic markers. Typically, genetic markers are bound by probes such as oligonucleotides or amplicons which specifically bind to unique variable regions of the genome. In some instances, the presence or absence of binding to a genetic marker identifies individuals by their unique nucleic acid sequence. In other instances, a marker binds to nucleic acid sequences of all individuals but the individual is identified by the position in the genome bound by a marker probe. The major causes of genetic variability are addition, deletion or point mutations, recombination and transposable elements within the genome of individuals in a plant population. The present invention may be applied to detecting and measuring genotypic variation. For example, polymorphisms, such as SNPs, which are represented by different sequences, may be detected.

In general, the present invention assay involves the following steps:

1. Preparing a biomolecule probe or microarray of probes bound to a solid phase (such as, for example, on plates, slides, wells, dishes, beads, particles, cups, strands, chips, and strips, both porous and non-porous) by spotting or synthesizing the biomolecule probe to a solid phase through standard chemical techniques;
2. Adding the target sample containing the first nucleic acid of interest to the immobilized second biomolecule probes and allowing RNA:DNA hybrids to form;
3. Adding a detectable entity specific for RNA:DNA hybrids (including RNA:DNA hybrid-specific antibodies or fragments thereof); and
4. Detecting the entity bound to the immobilized RNA:DNA hybrids.

Another embodiment of the present invention involves the following steps:

1. Preparing a biomolecule probe or microarray of probes bound to a solid phase (such as, for example, on plates, slides, wells, dishes, beads, particles, cups, strands, chips, and strips, both porous and non-porous) by spotting or synthesizing the biomolecule probe to a solid phase through standard chemical techniques;
2. Adding the target sample containing the first nucleic acid of interest to the immobilized second biomolecule probes and allowing RNA:DNA hybrids to form;
3. Adding an enzyme such as reverse transcriptase, preferably lacking RNAse H function and thermostable;
4. Incubating under conditions that promote reverse transcription which extends the sequence, thus forming a much longer RNA:DNA hybrid and enhancing antibody detection;
5. Adding a detectable entity specific for RNA:DNA hybrids (including RNA:DNA hybrid-specific antibodies or fragments thereof); and
6. Detecting the entity bound to the immobilized RNA:DNA hybrids.

A further embodiment of the present invention includes the following steps:

1. Preparing a biomolecule probe or microarray of probes bound to a solid phase (such as, for example, on plates, slides, wells, dishes, beads, particles, cups, strands, chips, and strips, both porous and non-porous) by spotting or synthesizing the biomolecule probe to a solid phase through standard chemical techniques;
2. Adding the target sample containing the first nucleic acid of interest to a second biomolecule probe bound to a microarray and a third unbound biomolecule probe;
3. Hybridizing the first target nucleic acid to a complementary region of the third biomolecule probe and allowing an RNA:DNA hybrid to form;
4. Hybridizing a non-hybridized portion of the RNA:DNA hybrid to an immobilized nucleic acid, forming an immobilized RNA:DNA hybrid complex;
5. Adding a detectable entity specific for RNA:DNA hybrids (including RNA:DNA hybrid-specific antibodies or fragments thereof); and
6. Detecting the entity bound to the immobilized RNA:DNA hybrid complexes.

Additionally, the third biomolecule probe may be a reagent-modified nucleic acid and the second immobilized nucleic acid may be an immobilized reagent-binding biomolecule, where the reagent-modified nucleic acid hybridizes to the first target nucleic acid and binds to the immobilized reagent-binding biomolecule. Non-limiting examples of reagents for modifying the nucleic acid include biotin, avidin, and streptavidin.

Yet another embodiment of the invention includes the following steps:

1. Preparing a biomolecule probe or microarray of probes bound to a solid phase (such as, for example, on plates, slides, wells, dishes, beads, particles, cups, strands, chips, and strips, both porous and non-porous) by spotting or synthesizing the biomolecule probe to a solid phase through standard chemical techniques;
2. Adding the target sample containing the first nucleic acid of interest to a second biomolecule probe bound to a microarray and a third unbound biomolecule probe;
3. Hybridizing the first target nucleic acid to a complementary region of the third biomolecule probe and allowing RNA:DNA hybrids to form;
4. Hybridizing the immobilized second biomolecule probe to a non-hybridized complementary region of the third biomolecule probe, forming an immobilized RNA:DNA hybrid complex;

5. Adding a detectable entity specific for RNA:DNA hybrids (including RNA:DNA hybrid-specific antibodies or fragments thereof); and
6. Detecting the entity bound to the immobilized RNA:DNA hybrid complex.

The present invention includes another embodiment with the following method steps:
1. Preparing a biomolecule probe or microarray of probes bound to a solid phase (such as, for example, on plates, slides, wells, dishes, beads, particles, cups, strands, chips, and strips, both porous and non-porous) by spotting or synthesizing the biomolecule probe to a solid phase through standard chemical techniques;
2. Adding the target sample containing the first nucleic acid of interest to a second biomolecule probe bound to a solid phase and a third unbound biomolecule probe;
3. Hybridizing a portion of the first target nucleic acid to a complementary region of the third unbound biomolecule probe and allowing RNA:DNA hybrids to form;
4. Hybridizing the solid phase-bound second biomolecule probe to a non-hybridized portion of the target nucleic acid, forming an immobilized RNA:DNA hybrid complex;
5. Adding a detectable entity specific for RNA:DNA hybrids (including RNA:DNA hybrid-specific antibodies or fragments thereof); and
6. Detecting the entity bound to the immobilized RNA:DNA hybrid complex.

A further embodiment of the present invention includes the following method steps:
1. Preparing a biomolecule probe or microarray of probes bound to a solid phase (such as, for example, on plates, slides, wells, dishes, beads, particles, cups, strands, chips, and strips, both porous and non-porous) by spotting or synthesizing the biomolecule probe to a solid phase through standard chemical techniques;
2. Adding the target sample containing the first nucleic acid of interest to a second biomolecule probe bound to a solid phase or immobilized nucleic acid, and a third unbound biomolecule probe;
3. Hybridizing the first target nucleic acid to the immobilized nucleic acid, forming an immobilized nucleic acid complex;
4. Hybridizing a third unbound biomolecule probe to the immobilized nucleic acid complex, forming an immobilized RNA:DNA hybrid complex;
5. Adding a detectable entity specific for RNA:DNA hybrids (including RNA:DNA hybrid-specific antibodies or fragments thereof); and
6. Detecting the entity bound to the immobilized RNA:DNA hybrid complex.

Another embodiment of the present invention includes the following steps:
1. Preparing a biological molecule or microarray of probes bound to a solid phase (such as, for example, on plates, slides, wells, dishes, beads, particles, cups, strands, chips, and strips, both porous and non-porous) by spotting or synthesizing the biomolecule probe to a solid phase through standard chemical techniques;
2. Adding the target sample containing the first nucleic acid of interest to a second biomolecule probe bound to a microarray and a third unbound detectably-labeled biomolecule probe;
3. Hybridizing the target nucleic acid to a second biomolecule probe bound to a solid phase, forming an immobilized RNA:DNA hybrid;
4. Hybridizing the third unbound detectably-labeled biomolecule probe to a non-hybridized portion of the bound second biomolecule probe;
5. Adding a detectable entity specific for RNA:DNA hybrids (including RNA:DNA hybrid-specific antibodies or fragments thereof); and
6. Separately detecting both the entity specific for RNA:DNA hybrids bound to the immobilized RNA:DNA hybrids and the detectably-labeled biomolecule probe.

In yet another embodiment of the invention, the method of detecting or quantifying a target nucleic acid involves the following steps:
1. Preparing a biological molecule or microarray of probes bound to a solid phase (such as, for example, on plates, slides, wells, dishes, beads, particles, cups, strands, chips, and strips, both porous and non-porous) by spotting or synthesizing the biomolecule probe to a solid phase through standard chemical techniques;
2. Adding the target sample containing the first nucleic acid of interest to a second biomolecule probe bound to a microarray and a third unbound detectably-labeled biomolecule probe;
3. Hybridizing a portion of the target nucleic acid to the second biomolecule probe bound to a solid phase, forming an immobilized RNA:DNA hybrid;
4. Hybridizing the third unbound detectably-labeled biomolecule probe to a non-hybridized portion of the target nucleic acid, forming an immobilized RNA:DNA hybrid complex;
5. Adding a detectable entity specific for RNA:DNA hybrids (including RNA:DNA hybrid-specific antibodies or fragments thereof); and
6. Separately detecting both the entity specific for RNA:DNA hybrids bound to the immobilized RNA:DNA hybrids and the detectably-labeled biomolecule probe.

A further embodiment of the present invention includes the following steps:
1. Preparing a biomolecule probe or microarray of probes bound to a solid phase (such as, for example, on plates, slides, wells, dishes, beads, particles, cups, strands, chips, and strips, both porous and non-porous) by spotting or synthesizing the biomolecule probe to a solid phase through standard chemical techniques;
2. Adding the target sample containing a first nucleic acid of interest to a second solid phase-bound biomolecule probe, and a third unbound detectably-labeled biomolecule probe to a fourth non-hybridized solid phase-bound biomolecule probe, where the fourth non-hybridized solid phase-bound biomolecule probe is different from the second solid phase-bound biomolecule probe;
3. Hybridizing the first target nucleic acid to a complementary region of the second solid phase-bound biomolecule probe and allowing RNA:DNA hybrids to form;
4. Hybridizing a complementary region of the third detectably-labeled biomolecule probe to the fourth non-hybridized solid phase-bound biomolecule probe;
5. Adding a detectable entity specific for RNA:DNA hybrids (including RNA:DNA hybrid-specific antibodies or fragments thereof); and
6. Separately detecting both the entity specific for RNA:DNA hybrids bound to the immobilized RNA:DNA hybrids and the detectably-labeled biomolecule probe. Specifically, a target nucleic acid hybridizes to a solid phase-bound biomolecule probe, forming an RNA:DNA hybrid. A different non-hybridized solid phase-bound biomolecule probe hybridizes to a complementary region of a detectably-labeled biomolecule probe. The target nucleic acid is detected and quantified by measuring the RNA:DNA hybrid using a detectable antibody specific for RNA:DNA hybrids and by measuring the detectably-labeled biomolecule probe.

The disclosed assay may be used to detect a plurality of different biological molecules of interest in a sample on a solid phase, where the solid phase is preferably a microarray. This is preferably accomplished by either screening for a sequence that is present in each of the target biological molecules of interest, or by screening with multiple probes that are collectively complementary to regions on the biological molecules of interest. The latter approach is preferred for use in detecting, for example, some diseases or predispositions to disease that are associated with numerous different mutations to particular genes, or genetic variations, including, but not limited to insertion or deletion mutations. The present invention also provides an assay which may be applied to a variety of applications, including, but not limited to gene expression, biological molecule (i.e. RNA, DNA, protein) detection on microarrays, mutation and polymorphism detection (i.e. SNP), and the like. In one particular embodiment, it is preferred to screen for sequences that are complementary to the regions of the mutant nucleic acid products of these genes that are characteristic of each of the mutations. Thus, one major advantage of this assay is the high-throughput application, enabling large screenings of a plurality of samples and potential diseases.

The disclosed method may also be used to determine the ratio of expression of different biological molecule species from individual organisms or an individual sample. For this purpose, the method is used to detect multiple species simultaneously. Microarray detection, as disclosed herein, is useful for this purpose. The disclosed method may also be used to detect similar or related biomolecule sequences where the related biological molecules have a common sequence motif between them, but which are otherwise different. For example, cells may contain multiple biological molecule species having similar regulatory sequences, similar structural motifs, or other sequences in common. Such classes of nucleic acid molecules may be detected with a single probe species by designing the probe to hybridize to the common sequence.

In the disclosed assay, an entity specific for RNA:DNA hybrids, including RNA:DNA hybrid-specific antibodies and their fragments, is utilized to detect biological molecules that have hybridized to the probe microarray rendering the labeling of the target biomolecules no longer necessary, but an option. In this approach, the longer the RNA:DNA hybrid, the greater the signal since a longer RNA:DNA hybrid may bind more antibody than a short RNA:DNA hybrid. Therefore, the longer the nucleic acid probe strands on the microarray, the more sensitive the detection of target nucleic acids or alternatively, the greater the signal intensity for a given amount of hybridized target nucleic acids. Unfortunately, it becomes more difficult and increasingly expensive to synthesize, prepare or utilize longer strands of probes in the preparation of these microarrays.

One disclosed embodiment of the present assay describes relatively short nucleic acid probe sequences bound to a solid substrate, minimizing the time, effort, and expense necessary to create the microarray. Target nucleic acid sequences in the sample are hybridized to these short probes creating a short RNA:DNA hybrid with a long nucleic acid tail. This short RNA:DNA hybrid probably only binds 1 or 2 RNA:DNA antibodies. When reverse transcriptase is added, and conditions are such that reverse transcriptase occurs, the nucleic acid probe portion of the RNA:DNA hybrid is extended to the length of the target nucleic acid strand, thus greatly increasing the length of the RNA:DNA hybrid. If the target nucleic acid strand were 1500 bases in length, then the resulting RNA:DNA hybrid would approach 1500 base pairs. An RNA:DNA hybrid of this length binds significantly more RNA:DNA antibodies, thereby greatly increasing the intensity of the signal produced, and increasing the sensitivity of detection of specific target nucleic acid sequences One disclosed embodiment is a method of detecting target nucleic acid sequences by reverse transcribing all or part of the bound nucleic acid probe sequence with a reverse transcriptase lacking an RNA:DNA hybrid-dependent exonuclease function (commonly referred to as an RNAse H function or component) and detecting the resulting RNA:DNA hybrid with an antibody specific for RNA:DNA hybrids. The nucleic acid probes are immobilized on a solid support in order to associate the RNA:DNA hybrid with the solid support. This allows for easy separation of hybrids form sample solution and specific detection of nucleic acid molecules based on the position of the hybrid on the solid support.

In one method of the present invention, reverse transcription is carried out using a reverse transcriptase, preferably a reverse transcriptase lacking RNAse H function. The reaction mixture including the nucleic acid molecule of interest, preferably in this embodiment, RNA; the hybridized immobilized nucleic acid primer; and the reverse transcriptase is then incubated under conditions to allow reverse transcription of the RNA molecule of interest and formation of DNA:RNA hybrids. Examples of reverse transcriptases that may be used in the disclosed method, or that may be adapted for use in the disclosed method are listed in Table 1. Preferred reverse transcriptases for use in the present method include reverse transcriptases, 18053-017, 18064-014 and 18064-071 from Life Technology; reverse transcriptases M5301 and M5302 from Promega; and reverse transcriptase 600085 from Strategene; each disclosed in Table 1.

TABLE 1

| SPECIFIC ACTIVITY | UNITS DEFINITION | PREPARATION FORM | ADDITIONAL ACTIVITIES | SUPPLIER CATALOG NO. |
|---|---|---|---|---|
| | 1 unit incorporates 1 nmol TTP into acid-insoluble form/10 min at 35° C. using poly(A).oligo dT$_{12-28}$ as substrate | 0.2 M KPO$_4$, 2 mM DTT, 0.2% Triton X-100, 50% glycerol, pH 7.2 | No detectable RNase, exonuclease | Adv Biotech AB-0321 AB-0321b |
| 26,700 U/mL | 1 unit incorporates 1 nmol dTMP into acid-precipitable form/10 min at pH 8.3, 37° C. | 200 mM KPO$_4$, 2 mM DTT, 0.2% Triton X-100, 50% glycerol, pH 7.2 | No detectable endonuclease, RNase | ACS Heidelb F00750S F00750M |

TABLE 1-continued

| SPECIFIC ACTIVITY | UNITS DEFINITION | PREPARATION FORM | ADDITIONAL ACTIVITIES | SUPPLIER CATALOG NO. |
|---|---|---|---|---|
| 10–20 U/μl | 1 unit incorporates 1.0 nmol [$^3$H]-JTTP into acid-insoluble products/10 min at 37° C. | 0.2 M KPO$_4$, 2.0 mM DTT, 0.2% Triton X-100, 50% glycerol, pH 7.2 | No detectable endonuclease, exonuclease, RNase | Amersham E 70041Y E 70041Z |
| >50,000 U/mg; >20,000 U/mL | 1 unit incorporates 1 nmol [$^3$H]-dTMP into acid-precipitable products/10 min at 37° C. using poly(A).d[pT]$_{15}$ as template primer | 200 mM KPO$_4$, 2 mM DTT, 0.2% Triton X-100, 50% glycerol, pH 7.2 | No detectable nonspecific RNases, nonspecific DNases (gel electrophoresis) | Boehringer 10911B 1495062 |
| 30,000 u/mL | 1 unit incorporates 1 nmol [$^3$H]-TMP into nucleic acid product/10 min at 37° C. | Solution containing 0.2 M KPO$_4$, 2.0 mM DTT, 0.2% Triton X-100, 50% glycerol, pH 7.2 | No detectable nonspecific nuclease | ICN 855928 855929 |
| 13 U/μL | 1 unit incorporates 1 nmol dTNP into a TCA-insoluble product/10 min at pH 8.3, 37° C. | 0.2 M KPO$_4$, 2 mM DTT, 0.2% Triton X-100, 50% glycerol, pH 7.2 | No detectable RNase, exogenous, nicking or degradation of RNA | NBL Gene 020704 |
| 30 U/μL | 1 unit incorporates 1 nmol dTNP into a TCA-insoluble product/10 min at pH 8.3, 37° C. | 0.2 M KPO$_4$, 2 mM DTT, 0.2% Triton X-100, 50% glycerol, pH 7.2; for high efficiency synthesis of full length cDNA in the 6–10 kilobase range | No detectable RNase, exonuclease, endonuclease, nicking | NBL Gene 020703 |
| >20,000 U/mg; 10,000–20,000 U/mL | 1 unit incorporates 1 nmol dNTP into DE-81 adsorbable form/10 min at 37° C. | 200 mM KPO$_4$, 2 mM DTT, 0.2% Triton X-100, 50% glycerol, pH 7.2 | No detectable RNase, DNase | Oncor 120111 120112 |
| 25,000–50,000 U/mg protein; 10,000–20,000 U/mL | 1 unit incorporates 1 nmol dTMP into acid-insoluble product/10 min at pH 8.3, 37° C. using poly(A)p[dT]$_{12–18}$ as template primer | Molecular biology grade; homogeneous purity; solution containing 0.2 M KPO$_4$, 2.0 mM DTT, 0.2% Triton X-100, 50% glycerol, pH 7.2 | No detectable RNase, DNase, nickase | Pharmacia 27-0922-01 27-0922-02 |
| 10,000–70,000 U/mL | 1 unit incorporates 1.0 nmol [$^3$H]-dTTP into acid-insoluble product/10 min at 37° C. | Purified; 20 mM KPO$_4$, 2 mM DTT, 0.2% Triton X-100, 50% glycerol, pH 7.2 | No detectable endonuclease, nonspecific RNase | Stratagene 600081 600082 |
| >40,000 U/mg; >20,000 U/mL | 1 unit incorporates 1 nmol TMP in acid-insoluble product/10 min at 37° C. with poly(A.[dT]$_{15}$ as substrate | Coomassie Blue shows a single band purity; 50 mM Tris.HCl, 10 mM DTT, 100 mM NaCl, 0.05% polydocanol, 1 mM EDTA, 50% glycerol, pH 8.4 | No detectable nonspecific RNases, nonspecific DNases (gel electrophoresis) | Boehringer 1062603 |
| 50–250 U/μL | 1 unit incorporates 1 nmol deoxynucleotides into acid-precipitable material/10 min at 37° C. using poly(rA).oligo[dT]$_{12–18}$ as template primer | >90% purity by SDS-PAGE; 20 mM Tris.HCl, 0.1 M NaCl, 0.1 mM EDTA, 1 mM DTT, 0.01% NP40, 50% glycerol, pH 7.5 | No detectable non-specific ss- and ds-endonuclease, exonuclease, RNase | Amersham E 70456Y E 70456Z |
| 50,000 U/mL | 1 unit incorporates 1 nmol TTP into acid-insoluble form/10 min at pH 8.0, 37° C. using poly(rA).oligo[dT] as template primer | 50 mM Tris.HCl, 0.1 mM DTT, 100 mM NaCl, 1 mM EDTA, 0.1% NP40, 50% glycerol, pH 8.3 | No detectable endonuclease, RNase | ACS Heldelb F00755S F00755M |
| 200 U/μL | 1 unit incorporates 1 nmol deoxyribonucleotide into acid-precipitable material/10 min at pH 8.3, 37° C. using poly(A)-oligo.[dT]$_{12–18}$ as template primer | Purity by SDS-PAGE, 250 mM Tris-HCl, 15 mM MgCl$_2$, 375 mM KCl, pH 8.3 and 100 mM DTT | No detectable RNase H | Life Technol 18053-017 |
| 200 U/μL | 1 unit incorporates 1 nmol deoxyribonucleotide into acid-precipitable material/10 min at pH 8.3, 37° C. using poly(A)-oligo.[dT]$_{12–18}$ as template primer | Purity by SDS-PAGE, 250 mM Tris-HCl, 15 mM MgCl$_2$, 375 mM KCl, pH 8.3 and 100 mM DTT | No detectable RNase H | Life Technol 18064-014 18064-071 |
| 200 U/μL | 1 unit incorporates 1 nmol deoxyribonucleotide into acid-precipitable material/10 min at pH 8.3, 37° C. using poly(A)-oligo.[dT]$_{12–18}$ as template primer | | | Life Technol 28025-013 28025-021 |
| 25,000 U/mL | 1 unit incorporates 10 nmol TTP into acid-insoluble material/10 min at 37° C. using poly(rA).oligo(dT) as template primer | 0.1 mM NaCl, 50 mM Tris.Hcl, 5 mM DTT, 1 mM EDTA, 0.1% NP40, 50% glycerol, pH 7.6 | No detectable endonuclease, RNase | NE Biolabs 253S 253L |
| ≧5000 U/mg protein | 1 unit incorporates 1.0 nmol [$^3$H]-TMP into acid-insoluble products/10 min at 37° C. using poly(A).d[pT]$^{15}$ as substrate | Recombinant; 99% by HPLC, SDS-PAGE; lyophilized containing 0.2% BSA as stabilizer | No detectable nuclease | Boehringer 1465333 |
| 20–40 U/μL | 1 unit incorporates 1 nmol deoxyribonucleotide into DE-81 absorbable form/10 min at 37° C. | Overproducer: 50 mM Tris.HCl, 0.1 M NaCl, 0.1% Triton X-100, 1 mM EDTA, 5 mM DTT, 50% glycerol, pH 8.3 | No detectable endo and exodeoxyribonucleases, RNases | Fermentas EP0351 EP0352 |
| 100–200 U/μL | 1 unit incorporates 1 nmol dTTP into acid-insoluble form/10 min at pH 8.3, 37° C. | Recombinant; ≧90% purity by SDS gel; 5X reaction buffer; 250 mM Tris.HCl, 375 mM KCl, 15 mM MgCl$_3$, 50 mM DTT, pH 8.3 | No detectable RNase H <1% DNase <3% RNase ≧90% supercoiled plasmid | Promega M5301 M5302 |
| | 1 unit incorporates 1 nmol TTP into acid-insoluble form/10 min at 37° C. using poly(A).oligo[dT]$_{11–18}$ as substrate | 50 mM Tris.HCl, 0.1 M NaCl, 1 mM EDTA, 5 mM DTT, 0.1% Triton X-100, 50% glycerol, pH 8.3 | No detectable RNase, exonuclease | Adv Biotech AB-0322 AB-0322b |

TABLE 1-continued

| SPECIFIC ACTIVITY | UNITS DEFINITION | PREPARATION FORM | ADDITIONAL ACTIVITIES | SUPPLIER CATALOG NO. |
|---|---|---|---|---|
| | 1 unit incorporates 1 nmol dTTP into acid-insoluble form/10 min at 37° C. | 50 mM Tris.HCl, 5.0 mM DTT, 1.0 mM EDTA, 0.1 M NaCl, 0.1% NP40, 50% glycerol, pH 8.0 | No detectable endocnulease, RNase | CHIMERx 1375-01 1375-02 |
| 35,000 U/mg | 1 unit incorporates 10 nmol dTTP into acid-insoluble material/10 min at pH 8.6, 37° C. using oligo.(dT)$_{12-18}$ primed poly(A)$_n$ as template | Solution containing 50% glycerol, 50 mM Tris.HCl, 0.1 M NaCl, 0.1 mM EDTA, 1 mM DTT, 0.1% Triton X-100, pH 7.5 | No detectable RNase, endonuclease, exonucleolytic DNase, protease | Epicentre M4425H M4410H |
| | 1 unit incorporates 1 nmol labeled dATP into acid-insoluble material/10 min at 37° C. | Solution containing 0.1 mM NaCl, 50 mM Tris.HCl, 1 mM EDTA, 5 mM DTT, 0.1% NP40, 50% glycerol, pH 8.0 | | ICN 152020 |
| | 1 unit incorporates 1 nmol TMP into DE-81 adsorbable form/10 min at 37° C. using polyA-oligodT$_{12-18}$ as substrate | 50 mM Tris.HCl, 0.1 M NaCl, 5 mM DTT, 1 mM EDTA, 0.1% Triton X-100, 50% glycerol, pH 8.3 | No detectable RNase, DNase | Oncor 120301 120302 |
| 50,000–95,000 U/mg protein; 10,000–20,000 U/mL | 1 unit incorporates 1 nmol dTMP into acid-insoluble product/10 min at pH 8.3, 37° C. using poly(rA).p[dT]$_{12-18}$ as template primer | Molecular biology grade; homogeneous purity; solution containing 50 mM Tris.HCl, 0.1 MNaCl, 1 mM EDTA, 5 mM DTT, 0.1% Triton X-100, 50% glycerol, pH 8.3 | No detectable RNase, DNase, nickase | Pharmacia 27-0925-01 27-0925-02 |
| 50,000 U/mL | 1 unit incorporates 1.0 nmol [$^3$H]TTP into acid-insoluble product/10 min at 37° C. | 50 mM Tris.HCl, 5 mM DTT, 1 mM EDTA, 100 mM NaCl, 0.1% NP40, 50% glycerol, pH 8.0 | No detectable RNase H, DNase, nonspecific RNase | Strategene 600085 |
| 10–30 U/μL | 1 unit incorporates 1 nmol [$^3$H]dTMP/10 min at 37° C. with poly(rA).oligo(dT) as template primer | 200 mM KPO$_4$, 2 mM DTT, 0.2% NP40, 50% glycerol, pH 7.2 | No detectable non-specific nuclease | Amersham E2610Y E2610Z |
| 400 U and 1600 U | 1 unit incorporates 1 nmol ($^3$H)dTMP/10 min at pH 8.3, 37° C. with poly(rA).oligo(dT) as template primer | Solution containing 200 mM KPO$_4$, 2 mM DTT, 0.2% NP40, 50% glycerol, pH 7.2 | No detectable nuclease | TaKaRa 2610 |
| | Transcriptase: 1 unit incorporates 4 nmol dTTP into acid insoluble material/30 min at pH 8.3, 45° C. using oligo(dT)18-primed poly(A)$_n$ as template; DNA Polymerase: 1 unit incorporates 10 nmol dNTP into acid insoluble material/30 min at pH 8.3, 74° C. | Solution containing 50% glycerol, 50 mM Tris.HCl, 0.1 M NaCl, 0.1 mM EDTA, 1 mM DTT, 0.5% Tween 20, 0.5% NP40, pH 7.5; no detectable DNA exo- and endonuclease, protease, RNase | | Epicentre Retrotherm ™ RT R19250 R19500 R1910H |
| | 1 unit incorporates 1 nmol dTTP into acid-insoluble form/10 min at 50° C. | 50 mM Tris.HCl, 5.0 mM DTT, 0.1 mM EDTA, 50% glycerol, stabilizers, pH 7.5 | No detectable endonuclease, 3'-exonuclease, 5'-exonuclease/5'-phosphatase, nonspecific RNase, ss- and ds-DNase | CHIMERx 1374-01 1374-02 |

Reverse transcription may generally be performed at any temperature within the functional temperature range of the reverse transcriptase. Preferably, the temperature of incubation is any temperature at which the reverse transcriptase is functional and the primer remains hybridized to the target nucleic acid molecule. For non-thermophilic reverse transcriptases, preferred temperatures are those temperatures that are at or around the optimum temperature for the reverse transcriptase. For most non-thermophilic reverse transcriptases this temperature will be between about 25° C. and 45° C.

In a preferred embodiment, a thermophilic reverse transcriptase is used for increasing selectivity. The highest temperature at which a thermophilic reverse transcriptase is functional may be quite high. For this reason, preferred temperature ranges for reverse transcription when a thermophilic reverse transcriptase is used are most conveniently described in terms of the calculated melting temperature of a hybrid between the RNA molecule of interest and the primer. Such a melting temperature is referred to herein as the RNA/primer melting temperature (R/P Tm). Preferred ranges include a temperature from 20° C. below the melting temperature of a hybrid between the RNA molecule of interest and the primer and 5° C. above the melting temperature of a hybrid between the RNA molecule of interest and the primer. Other preferred ranges when using a thermophilic reverse transcriptase include those listed in Table 2.

TABLE 2

| MAX: | to R/P Tm | to 5° C. below R/P Tm | to 3° C. below R/P Tm |
|---|---|---|---|
| 1 | 20° C. below R/P Tm | 20° C. below R/P Tm | 20° C. below R/P Tm |
| 2 | 15° C. below R/P Tm | 15° C. below R/P Tm | 15° C. below R/P Tm |
| 3 | 10° C. below R/P Tm | 10° C. below R/P Tm | 10° C. below R/P Tm |
| 4 | 7° C. below R/P Tm | 7° C. below R/P Tm | 7° C. below R/P Tm |
| 5 | 5° C. below R/P Tm | 5° C. below R/P Tm | 5° C. below R/P Tm |
| 6 | 3° C. below R/P Tm | 3° C. below R/P Tm | 3° C. below R/P Tm |

It is specifically noted that every specific, but unnamed, range within the enumerated ranges above is contemplated as an alternative preferred range. Preferred temperatures for reverse transcription include about 20° C. below R/P Tm, about 15° C. below R/P Tm, about 12° C. below R/P Tm, about 10° C. below R/P Tm, about 7° C. below R/P Tm, about 5° C. below R/P Tm, about 3° C. below R/P Tm, 20° C. below R/P Tm, 15° C. below R/P Tm, 12° C. below R/P Tm, 10° C. below R/P Tm, 7° C. below R/P Tm, 5° C. below R/P Tm, and 3° C. below R/P Tm. In general, the closer the temperature is to the R/P Tm, the greater the degree of discrimination there will be between specific and non-specific hybrids of the RNA and primer. If the temperature is close to the R/P Tm, however, decreased stability of specific hybrids may cause priming to be less efficient.

R/P Tm may be determined either by calculation or by empirical measurement. For calculating R/P Tm, any established formula for calculating stability of nucleic acid hybrids may be used. A preferred formula for calculating R/P $$Tm \text{ is } Tm = \frac{\Delta H}{\Delta S + R \times \ln(C/4)} + 16.6 \, \log\frac{[K^+]}{1 + 0.7[K^+]} - 237.15,$$

which was derived from studies on the stability of perfectly-matched DNA:DNA hybrids. For RNA:DNA hybrids, incorporating formamide concentration in the formula does not hold because the relationship between formamide concentration and the depression of Tm is not linear. At 80% formamide, RNA:DNA hybrids are more stable than DNA:DNA hybrids, increasing the Tm by about 10 to 30° C. depending on the sequence (Hames & Higgins, *Nucleic Acid Hybridisation: A Practical Approach* (IRL Press Limited, Oxford, England. 1985)). Carrying out the reaction in 80% formamide may therefore also be used to suppress formation of DNA:DNA duplexes, to preferentially select RNA:DNA hybrids, and to estimate the Tm for R/P. Because the empirically derived formulas for the estimation of RNA:DNA hybrid Tm may not be as accurate for short nucleic acid primers, the hybridization temperature is preferably determined by assessing hybrid stability in 0.1–0.4 M monovalent cation at temperatures ranging from 40 to 60° C. R/P Tm may also be determined empirically (Lesnick and Freier, *Biochemistry* 34:10807–10815 (1995), McGraw et al., *Biotechniques* 8:674–678 (1990), and Rychlik et al., *Nucleic Acids Res.* 18:6409–6412 (1990)).

As used herein, a thermophilic reverse transcriptase is any reverse transcriptase that retains at least 5% of its maximum activity at any temperature above 50° C. or which has an optimal temperature of at least 50° C. Preferred reverse transcriptases are those which have an optimal temperature of at least 50° C. As used herein, maximum activity of a reverse transcriptase is defined as the activity, as measured in the assay described below, that a given reverse transcriptase exhibits at its optimal temperature. As used herein, optimal temperature of a reverse transcriptase is defined as the temperature at which the activity of the reverse transcriptase is greatest, as measured in the assay described below. The optimal temperature for a given reverse transcriptase may be determined by measuring its activity in the following assay at various temperatures. In general, an optimal temperature need be determined only to within a range so that assays need only be performed at intervals of 5 to 10 degrees.

Methods for immobilization of nucleic acid sequences to solid phase substrates are well established. Oligonucleotides, including half probes and rolling circle replication primers, may be coupled to substrates using established coupling methods. For example, attachment methods are described by Pease et al., *Proc. Natl. Acad. Sci. USA* 91(11):5022–5026 (1994), and Khrapko et al., *Mol. Biol (Mosk) (USSR)* 25:718–730 (1991). A method for immobilization of 3'-amine oligonucleotides on casein-coated slides is described by Stimpson et al., *Proc. Natl. Acad. Sci. USA* 92:6379–6383 (1995). A preferred method of attaching oligonucleotides to solid-state substrates is described by Guo et al., Nucleic Acids Res. 22:5456–5465 (1994).

The immobilization and arraying of nucleic acids or primer molecules to solid supports may be accomplished using any suitable technique. For example, immobilization may be accomplished either by in situ nucleic acid synthesis (Maskos and Southern, *Nucleic Acids Research*, 20:1679–1684 (1992); Pease et al., *Proc. Natl. Acad. Sci. USA,* 91:5022–5026 (1994)) or by covalent or passive attachment of chemically synthesized oligonucleotides (Guo et al., *Nucleic Acids Research,* 22:5456–5465 (1994)), or by covalent or passive attachment of other nucleic acids, amplicons, cDNAs, and the like, in combination with robotics arraying technologies. Other immobilization techniques are described in U.S. Pat. No. 5,412,087 to McGall et al., U.S. Pat. No. 5,429,807 to Matson et al., and U.S. Pat. No. 5,510,087 to Fodor et al. Thousands of different primers may be arrayed onto a small area on a solid support to interrogate thousands of target nucleic acid molecules. The density of nucleic acids or primers should be matched with the method of arraying and the means of detection.

One embodiment of the present invention comprises hybridization of target nucleic acid sequences to the universal array comprising specific nucleic acid probes, wherein a "universal array" or "universal array sequences", herein interchangeably defined as short nucleic acid sequences of every possible base combination. The universal array sequences comprise a range of 6–10 bases, preferably 5–6 bases, wherein the number of possible combinations (i.e. different probes bound to the solid phase) is 1024 and 4096, respectively, and enable nucleic acid expression analysis, wherein the result may be used as a fingerprint, in which different tissues or samples give different fingerprints.

The embodiments comprising a third nucleic acid probe may be immobilized to the solid phase array by using "capture tags". As used herein, a capture tag is any compound that may bind to another compound or moiety. The primer is thus immobilized through binding of an attached capture tag to its binding partner. Such binding partners are referred to herein as "capture docks". A capture tag is a compound, such as a ligand or hapten, that binds to or interacts with another compound, such as ligand-binding molecules or an antibody. It is also preferred that such interaction between the capture tag and the capture dock be a specific interaction, such as between a hapten and an antibody or a ligand and a ligand-binding molecule.

A further embodiment of this assay comprises a capture tag with two adjacent regions: a target nucleic acid-specific region and a "capture sequence complement". As used herein, a "capture sequence complement" comprises nucleic acid sequence which is complementary to "universal capture sequences" immobilized to the solid phase microarray, wherein "universal capture sequences" refer to short nucleic acid sequences which are known and their location on the solid phase microarray are predetermined. The capture tag or probe comprising a "capture sequence complement" may be immobilized to the solid phase microarray by hybridizing to its complementary "universal capture sequence".

In another embodiment of the present invention, the "capture tag" refers to a labeled nucleic acid probe which hybridizes to its "capture dock" which is bound to the solid phase microarray, wherein the capture dock is a common sequence specific for the labeled nucleic acid probe.

Alternative capture tags include hapten or ligand molecules that may be coupled to oligonucleotides. Capture tags, described in the context of nucleic acid probes, have been described by Syvnen et al., *Nucleic Acids Res.*, 14:5037 (1986). Capture tags also include biotin, which may be incorporated into nucleic acids.

Adhering or coupling primers to a substrate may be accomplished by adhering or coupling capture docks to the substrate. The capture docks mediate adherence of a primer by binding to, or interacting with, a capture tag on the primer. Capture docks immobilized on a substrate allow capture of the primer on the substrate. By attaching different capture docks to different regions of a substrate different capture tags attached to different primers, may be captured at different, and therefore diagnostic, locations on the substrate. For example, in a microtiter plate multiplex assay, capture docks specific for up to 96 different capture tags may be immobilized on a microtiter plate, each in a different well. Capture and detection will occur only in those wells corresponding to capture tags for which the corresponding nucleic acid molecules were present in a sample.

In one embodiment, the capture dock is an oligonucleotide. Methods for immobilizing and coupling oligonucleotides to substrates are well established. For example, attachment methods are described by Pease et al., *Proc. Natl. Acad. Sci. USA* 91(11):5022–5026 (1994), and Khrapko et al., *Mol Biol (Mosk) (USSR)* 25:718–730 (1991). A method for immobilization of 3'-amine oligonucleotides on casein-coated slides is described by Stimpson et al., *Proc. Natl. Acad. Sci. USA* 92:6379–6383 (1995). Another method of attaching oligonucleotides to solid phase substrates is described by Guo et al., *Nucleic Acids Res.* 22:5456–5465 (1994).

Methods for immobilizing proteins to substrates are well established. Immobilization may be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides, maleimides and glutaraldehyde. These and other attachment agents, as well as methods for their use in attachment, are described in *Protein immobilization: Fundamentals and Applications*, Richard F. Taylor, ed. (M. Dekker, New York, 1991), Johnstone and Torpe, *Immunochemistry In Practice* (Blackwell Scientific Publications, Oxford, England, 1987) pages 209–216 and 241–242, and *Immobilized Affinity Ligands*, Craig T. Hermanson et al., eds. (Academic Press, New York, 1992). Proteins may be attached to a substrate by chemically cross-linking a free amino group on the antibody to reactive side groups present within the substrate. For example, proteins may be chemically cross-linked to a substrate that contains free amino or carboxyl groups using glutaraldehyde or carbodiimides as cross-linker agents. In this method, aqueous solutions containing free proteins are incubated with the solid-state substrate in the presence of glutaraldehyde or carbodiimide. Standard immobilization chemistries are known by those of skill in the art.

In another embodiment, the sensitivity of the disclosed method is increased by repeated washing of the hybrid sample to remove free non-hybridized nucleic acids present in the sample. It is useful to remove the non-specific non-hybridized nucleic acid because secondary structures in the nucleic acid may be recognized by the detection means, resulting in elevated assay background.

The preferred hybridization sample nucleic acid detection kits for use with the disclosed method may be made using some or all of the components required for the method. The kit preferably contains a microarray solid support having a plurality of sample detection sites or elements, to which a nucleic acid is immobilized and the nucleic acid is complementary to a target nucleic acid or part thereof, or the nucleic acid being complementary to part of the RNA:DNA hybrid, or said nucleic acid being complementary to a nucleic acid probe; a hybridization buffer that allows and/or enhances hybridization of the nucleic acids; a wash buffer that removes any excess non-hybridized molecules without affecting the hybridized molecules; and a solution comprising an RNase and a detection antibody specifically reactive with an RNA:DNA hybrid, where the RNase degrades the non-hybridized or single-stranded RNA.

Preferably kits contain all or some of the following components: a sample transport medium for stabilization of the sample; a solid phase bound microarray of biomolecules specific for a second biomolecule to be detected; hybridization buffer; entity specific for RNA:DNA hybrids; wash buffer; enhance buffer; and the reagents necessary for detecting the RNA:DNA hybrid-specific antibody. In addition, some kits may include a thermostable reverse transcriptase lacking RNA:DNA hybrid-dependent exonuclease (RNAse H) function. A further composition of the kits may include a nucleic acid probe comprising a capture sequence complement region. In addition, the kits may also include a labeled biomolecule probe which hybridizes to a common sequence of the solid phase bound biomolecule. Kits may further comprise, but are not limited to, a universal array of biological molecules for the detection of a sample biomolecule. Kits may comprise all of these components, or a portion thereof.

For amplified-antibody detection, in addition to the reagents included in the hybridization kits for direct detection described above, the following reagents comprising all or part may also be included in the kits: detectably-labeled anti-mouse IgG; biotinylated anti-mouse IgG; labeled anti-mouse streptavidin; biotinylated anti-streptavidin; or acetylated BSA solution.

The kits should contain a negative control and a positive control. Preferably, probes for the negative and positive controls are included on the microarray solid phase with the nucleic acid sequences.

The following non-limiting examples illustrate use of the present assay and kits.

EXAMPLES

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein may be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

Example 1

Detection of RNA:DNA Hybrids on Probe Microarrays

The following is an example of a preferred method of performing one embodiment of the disclosed method for the detection of target biomolecule sequences in a sample.

In general, the assay is preferably used to detect a sample size of 0.05 µg of nucleic acids. Most preferably, 0.05 µg–10 µg of total nucleic acids is detected using the assay of the present invention.

The target nucleic acid sample was resuspended in nuclease-free water and added to hybridization buffer. The hybridization solution was denatured at 95° C. for 2–5 minutes. The hybridization solution containing the target nucleic acid was added to the glass slide which has a microarray of oligonucleotides spotted. Hybridize at 65° C. for 16–20 hours. Follow by either direct detection or amplified detection.

For direct detection, the glass slide with a microarray of primers bound to the surface was washed 3 times for 1–2 minutes with 1×PBS/0.05% Tween 20™ and shaken on a rotary shaker (1100 rpm). The RNA:DNA antibody staining solution was added so that the final concentration was 0.144 µg/µl. The glass slide microarray was incubated in solution for 1 hour at room temperature shaking (1100 rpm). The glass slide was washed with 1×PBS/0.05% Tween 20™ and shaken (1100 rpm) for 15 minutes at room temperature. The microarray was then incubated in a mouse antibody, specifically directed against Cy3 or Cy5, staining solution at room temperature and shaken for 1 hour at 1100 rpm. A number of fluorescent dyes may be used, such as, but not limited to Cy3 or Cy5. The final concentration of the Cy-dye was 0.04 µg/µl in a solution of 10% goat serum and 1×PBS/0.05% Tween 20™. Using slightly rigorous means, the slide was washed four times for approximately 10 seconds each in wash buffer. The slide was then incubated at 53° C. for 15 minutes in enhance buffer. The slide was then washed in wash buffer four times for approximately 10 seconds each, using mildly rigorous means. The microarray bound to the glass slide was dried by centrifugation at 2000 rpm for 7–10 minutes, or until dry. The results were analyzed by reading the slide in an array scanner (Affymetrix 417 Array Scanner or equivalent) with photo excitation at 532 mn and 635 nm, for scanning slides developed with Cy3 and Cy5 labeled antibodies, respectively.

For amplified detection, the slide was washed 3 times for 1–2 minutes in 1×PBS/0.05% Tween 20™, shaken on a rotary shaker at 1100 rpm. The slide was incubated in RNA:DNA hybrid-specific antibody staining solution for 1 hour shaking (1100 rpm) at room temperature. The final concentration of RNA:DNA antibody staining solution was 0.144 µg/µl. The slide was washed in 1×PBS/0.05% Tween 20™ for 15 minutes at room temperature shaking (1100 rpm). The spotted slide was covered with biotinylated mouse IgG antibody from goat staining solution and incubated for 10 minutes at room temperature. The microarray was washed 2 times for 1–2 minutes each in 1×PBS/0.05% Tween 20™. The spotted slide was covered with goat anti-mouse R-phycoerythrin streptavidin (0.01 µg/µl; SA-PE) staining solution and incubated for 10 minutes at room temperature. Washing was repeated as described above. The spotted slide was covered with biotinylated goat antibody raised against streptavidin (0.5 mg/mL) staining solution and incubated for 10 minutes at room temperature. The slide was again incubated with goat anti-mouse R-phycoerythrin streptavidin (0.01 µg/µl; SA-PE) staining solution for ten minutes at room temperature. The slide was then washed 3 times for 1–2 minutes in 1×PBS/0.05% Tween 20™. The microarray was then dried by centrifugation at 2000 rpm for 7–10 minutes, or until dry. The results were analyzed by reading slide in an array scanner or equivalent (Affymetrix 417 Array Scanner), with photo excitation at 532 nm and 635 nm, for scanning slides developed with Cy3 or PE and Cy5 labeled antibodies respectively.

Example 2

Labeled Oligonucleotide Hybridization Prior to Sample Hybridization

A Cy3 or Cy5 labeled n-mer oligonucleotide was added to a hybridization buffer containing SSC and SDS and was denatured at 95° C. for 2–5 minutes. A number of fluorescent dyes may be used, such as, but not limited to Cy3 and Cy5. The glass slide comprising spotted oligonucleotides was covered with the hybridization solution and incubated at room temperature for 20 seconds. The coverslip was removed with rigorous dunks in 2×SSC/0.2% SDS. Any residual SDS was washed off by dunking the slide in 0.05×SSC for 30 seconds. The slide was dried by centrifugation at 2000 rpm for 7–10 minutes or until dry. The glass slide was then read in an array scanner (Affymetrix 417 Array Scanner or equivalent), with photo excitation at 532 nm and 635 nm, for scanning slides developed with Cy3 and Cy5 labeled oligonucleotides, respectively, for analysis. Sample hybridization followed.

Example 3

Detection of RNA Mediated by Reverse Transcriptase Lacking RNAse H Function

The following is an example of a method of performing one embodiment of the disclosed method for the detection of target nucleic acid sequences in a sample.

The 5 prime biotinylated 20 to 30 nucleotide primers was mixed with a streptavidin coated solid phase and incubated for 30 to 60 minutes at 20–27° C. with constant shaking (1100 rpm). A sample of target nucleic acids was added to the solid phase. Hybridization/extension buffer (100 mM Tris-HCl, pH 8.3, 150 mM KCl, 6 mM $MgCl_2$, 20 mM DTT, and 1 mM each dNTP) was then added. The target nucleic acid and primer were annealed by heating the mixture to the optimal annealing temperature, preferably 60° C. (optimal annealing temperature varies with primer and nucleic acid utilized), for 20–30 minutes. The mixture was then cooled at 20–27° C. for 10 minutes. Additional hybridization/extension buffer and reverse transcriptase, preferably thermostable and lacking RNAse H, was added. The reaction was incubated for 30–60 minutes at 42° C. EDTA (0.5 M) was added and incubated for 30 minutes at 37° C. RNA:DNA hybrid-specific alkaline phosphatase conjugated antibody mix was added and incubated at 20–27° C. for 30–60 minutes. Any unbound antibody was washed away, followed by the addition of a chemiluminescent substrate. The solution was incubated for 15–30 minutes at 20–27° C. The signal which was emitted was read with a luminometer at the appropriate wavelength.

Example 4

Binding of RNA:DNA Hybrid-Specific Antibodies

Hybridized RNA:DNA samples were incubated with the antibodies for a sufficient amount of time to allow conjugation of the hybrids. The hybrids were bound to the antibodies by incubation for 5 minutes to 24 hours at 15 to 65° C. on a platform shaker with a shaking speed of 0 to 1500 rpm. Preferably, the incubation time was 30 to 120 minutes at 20 to 40° C., with shaking at 300 to 1200 rpm. Most preferably, binding occurred with incubation at one hour at room temperature with vigorous shaking on a rotary platform shaker with a rotary shaking speed between approximately 300 and 1000 rpm. It will be understood by those skilled in the art that the incubation time, temperature, and shaking may be varied to achieve alternative capture kinetics as desired.

Example 5

Figure 6A:
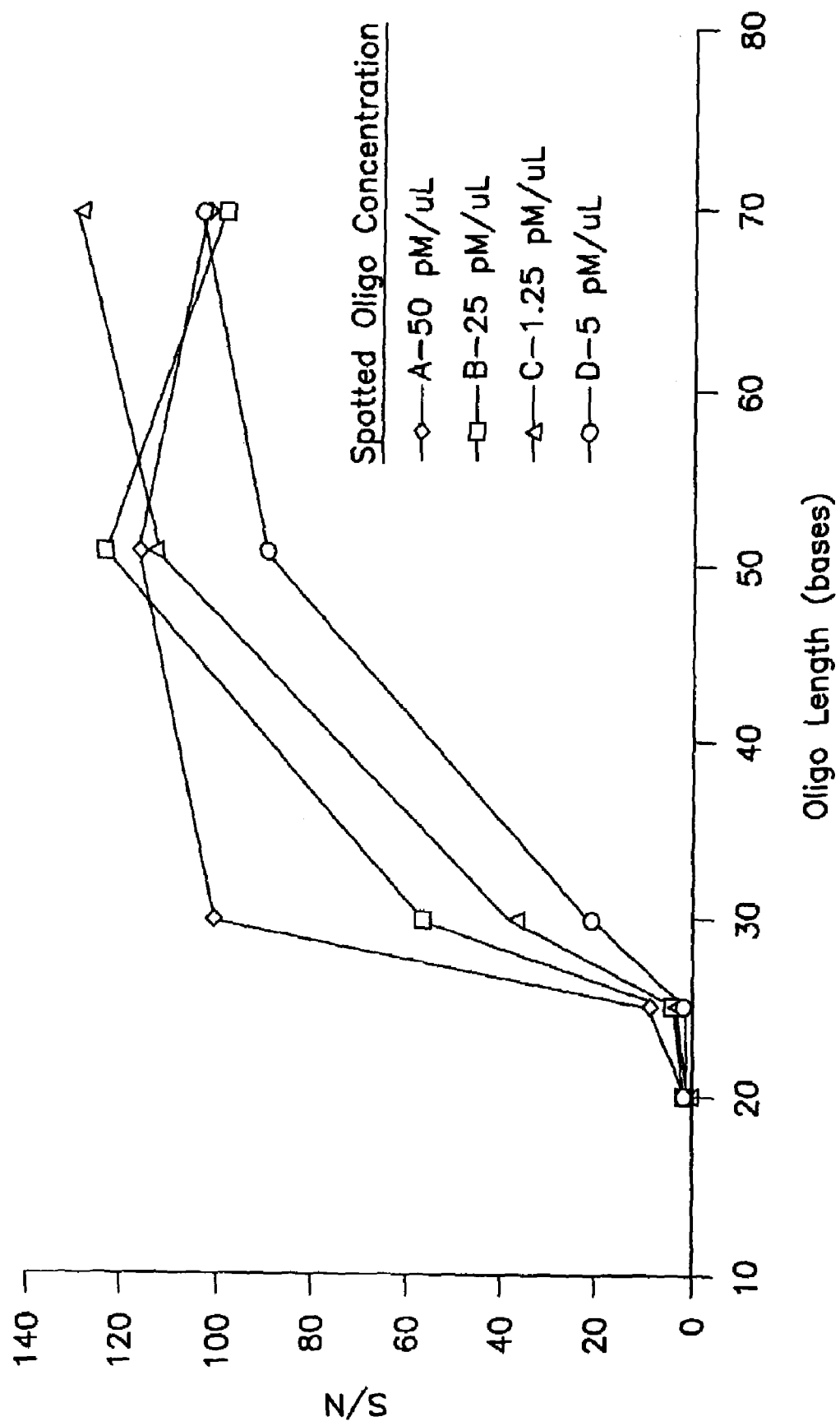
FIGS. 6A–B are graphs representing a solid phase-bound oligonucleotide length comparison using detection with a monoclonal antibody (FIG. 6A) and a polyclonal antibody (FIG. 6B) as a function of signal to noise ratio of the microarray.

Oligonucleotide Length Comparison Detected by Monoclonal and Polyclonal Antibody A single oligonucleotide of varying length was spotted at four different concentrations in replicates of ten. The spotted 72-mer oligonucleotide was part of IMAGE clone # 259983 which corresponds to the 40S Ribosomal protein S11. The shorter oligonucleotides were sequential truncations of the parent 72-mer. These microarrays were hybridized to varying concentrations of complementary RNA and were visualized using the monoclonal primary RNA:DNA hybrid antibody. At a target concentration of 800 pM, substantial signal was observed at an oligonucleotide length of 30 bases, but there was a drop in signal at 25 bases. FIG. 6A shows the results of the signal to noise ratio as a function of oligonucleotide length at an RNA concentration of 800 pM with various spotted oligonucleotide concentrations upon RNA:DNA hybrid-specific monoclonal antibody detection.

The polyclonal antibody detection protocol was the same as that described above for the monoclonal antibody, with the exception that a Cy3-labeled goat secondary antibody from rabbit was used instead of the mouse antibody from goat. The results (FIG. 6B) with the polyclonal antibody showed significantly improved detection compared to the monoclonal antibody for oligonucleotides less than 30 bases in length. For oligonucleotides greater than 30 bases, there was no significant difference in signal.

Figure 6B:
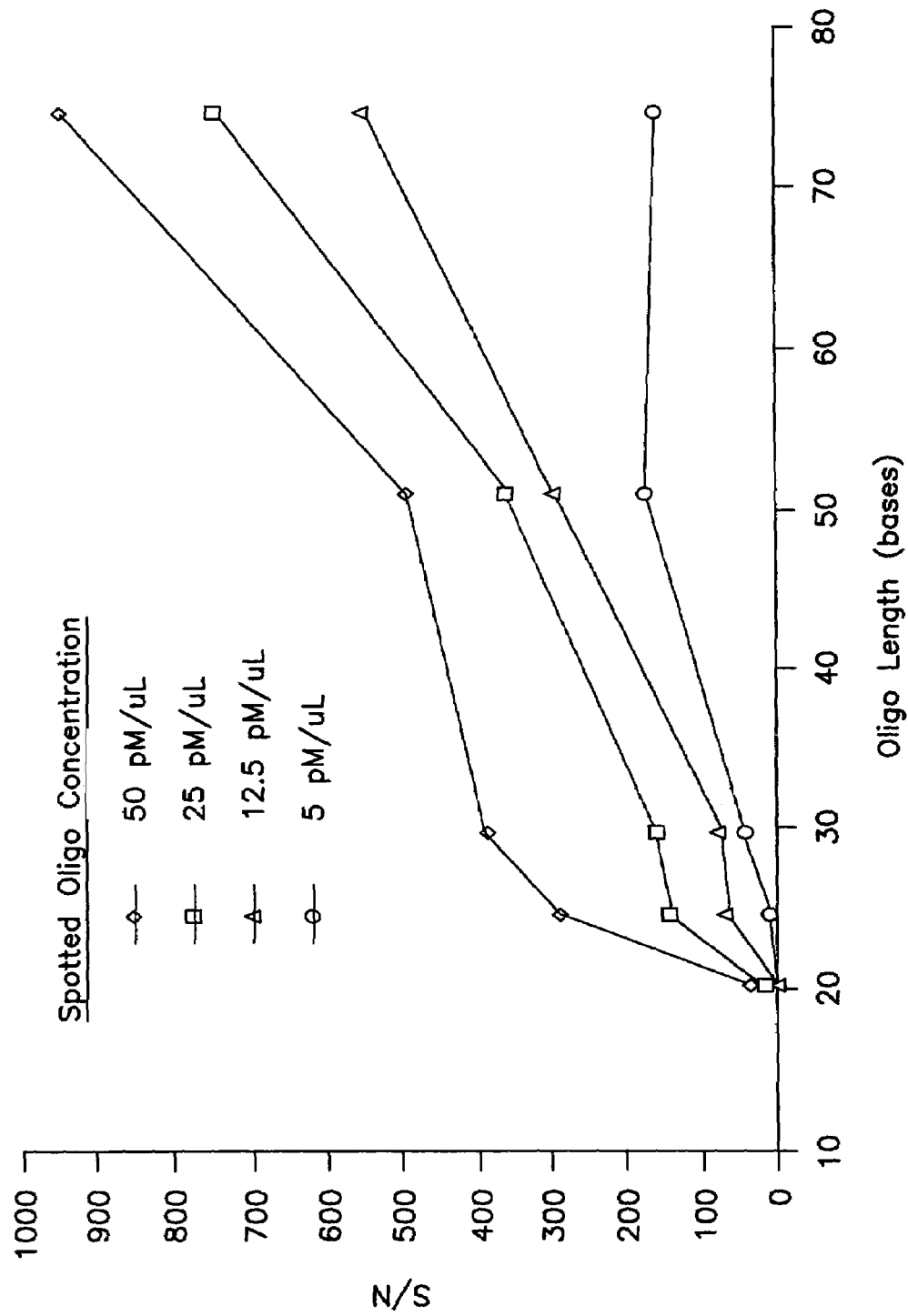

The polyclonal RNA:DNA antibody provided a significantly more sensitive method for detecting RNA:DNA hybrids that are less than 30 base pairs long as compared to detection with the monoclonal antibody (see FIGS. 6A–B).

The contents of all patents, patent applications, published PCT applications and articles, books, references, reference manuals and abstracts cited herein are hereby incorporated by reference in their entirety to more fully describe the state of the art to which the invention pertains.

As various changes may be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. A method for detecting or quantifying a target nucleic acid on a microarray having a plurality of sample detection sites, comprising:
    (a) hybridizing the target nucleic acid to a microarray-bound biomolecule probe, forming an immobilized RNA:DNA hybrid;
    (b) hybridizing a detectably-labeled biomolecule probe to a non-hybridized portion of the microarray-bound biomolecule probe, forming an immobilized RNA:DNA hybrid complex comprising the target nucleic acid, a detectably-labeled biomolecule probe, and a microarray-bound biomolecule probe;
    (c) detecting the target nucleic acid by measuring the immobilized RNA:DNA hybrid complex by binding the complex to a detectable antibody specifically reactive with an RNA:DNA hybrid;
    (d) detecting the detectably-labeled biomolecule probe; and
    (e) repeating steps (a)–(c) on each of the plurality of sample detection sites, wherein the detectably-labeled biomolecule probe is distinguishable from the detectable antibody.

2. The method according to claim 1, wherein the repeating steps are carried out sequentially.

3. The method according to claim 1, wherein the repeating steps are carried out simultaneously.

4. A method for detecting or quantifying a target nucleic acid on a microarray having a plurality of sample detection sites, comprising:
    (a) hybridizing a portion of the target nucleic acid to a microarray-bound biomolecule probe, forming an immobilized RNA:DNA hybrid;
    (b) hybridizing a non-hybridized portion of the target nucleic acid to a detectably-labeled complementary nucleic acid probe, forming an immobilized RNA:DNA hybrid complex comprising the target nucleic acid, a detectably-labeled biomolecule probe, and a microarray-bound biomolecule probe; and
    (c) detecting the target nucleic acid by measuring the immobilized RNA:DNA hybrid complex by binding the complex to a detectable antibody specifically reactive with an RNA:DNA hybrid and the detectably-labeled biomolecule probe; and
    (d) repeating steps (a)–(c) on each of the plurality of sample detection sites.

5. The method according to claim 4, wherein the repeating steps are carried out sequentially.

6. The method according to claim 4, wherein the repeating steps are carried out simultaneously.

7. A method for detecting or quantifying a target nucleic acid on a microarray having a plurality of sample detection sites, comprising:
    (a) hybridizing the target nucleic acid to a complementary nucleic acid probe, forming an RNA:DNA hybrid;
    (b) hybridizing a non-hybridized portion of the target nucleic acid to a microarray-bound biomolecule probe, forming an immobilized RNA:DNA hybrid complex comprising the target nucleic acid, a detectably-labeled biomolecule probe, and a microarray-bound biomolecule probe; and (c) detecting the target nucleic acid by measuring the RNA:DNA hybrid complex by binding the complex to a detectable antibody specifically reactive with an RNA:DNA hybrid; and (d) repeating steps (a)–(c) on each of the plurality of sample detection sites.

8. The method according to claim 7, wherein the repeating steps are carried out sequentially.

9. The method according to claim 7, wherein the repeating steps are carried out simultaneously.

10. A method for detecting or quantifying a target nucleic acid on a microarray having a plurality of sample detection sites, comprising:
(a) hybridizing the target nucleic acid to an immobilized reagent-modified nucleic acid to form an immobilized reagent-modified RNA:DNA hybrid, wherein the immobilized reagent-modified nucleic acid is bound to an immobilized reagent-binding molecule;
(b) detecting the target nucleic acid by measuring the immobilized RNA:DNA hybrid using a detectable antibody specifically reactive with the RNA:DNA hybrid; and
(c) repeating steps (a)–(b) on each of the plurality of sample detection sites.

11. The method according to claim 10, wherein the repeating steps are carried out sequentially.

12. The method according to claim 10, wherein the repeating steps are carried out simultaneously.

13. A method for detecting or quantifying a target nucleic acid on a microarray having a plurality of sample detection sites, comprising:
(a) hybridizing a target nucleic acid to a microarray-bound biomolecule probe, forming an RNA:DNA hybrid;
(b) hybridizing a non-hybridized microarray-bound biomolecule to a complementary region of a detectably-labeled biomolecule probe, wherein said non-hybridized microarray-bound biomolecule probe is different from the microarray-bound biomolecule probe of step (a);
(c) detecting the target nucleic acid by measuring the RNA:DNA hybrid by binding the RNA:DNA hybrid to a detectable antibody specifically reactive with the RNA:DNA hybrid;
(d) detecting the detectably-labeled biomolecule probe; and
(e) repeating steps (a)–(c) on each of the plurality of sample detection sites.

14. The method according to claim 13, wherein the repeating steps are carried out sequentially.

15. The method according to claim 13, wherein the repeating steps are carried out simultaneously.

16. A kit for the detection of an RNA:DNA hybrid comprising:
a) a microarray solid support having a plurality of sample detection spots, wherein said sample detection spots are immobilized nucleic acids, said immobilized nucleic acid being complementary to a target nucleic acid or part thereof, or said immobilized nucleic acid being complementary to part of an RNA:DNA hybrid, or said immobilized nucleic acid being complementary to a nucleic acid probe;
b) a hybridization buffer;
c) a wash buffer;
d) a solution comprising an RNase and a detection antibody specifically reactive with an RNA:DNA hybrid; and
e) a biomolecule probe, wherein said probe is a detectably-labeled biomolecule or nucleic acid probe that hybridizes to a portion of the immobilized nucleic acid of (a) but not to that portion complementary to the target nucleic acid, or wherein said probe is a nucleic acid probe complementary to a target nucleic acid.

17. The kit according to claim 16, wherein the detection antibody is a labeled RNA:DNA hybrid-specific antibody.

18. The kit according to claim 16, wherein the detection antibody is an RNA:DNA hybrid-specific antibody and a labeled RNA:DNA hybrid antibody-specific antibody.

19. The kit according to claim 17, wherein the RNA:DNA hybrid-specific antibody is monoclonal.

20. The kit according to claim 18, wherein the labeled RNA:DNA hybrid antibody-specific antibody is monoclonal.

21. The kit according to claim 17, wherein the RNA:DNA hybrid-specific antibody is polyclonal.

22. The kit according to claim 18, wherein the labeled RNA:DNA hybrid antibody-specific antibody is polyclonal.

23. A kit for detecting or quantifying a target nucleic acid on microarray, comprising:
a) a microarray solid support having a plurality of sample detection spots, wherein said sample detection spots are immobilized biomolecule probes complementary to a target nucleic acid or part thereof,
b) a detectably labeled biomolecule probe that hybridizes to a portion of the immobilized biomolecule probe of (a) but not to that portion complementary to the target nucleic acid; and
c) a solution comprising an RNase and a detection antibody specifically reactive with an RNA:DNA hybrid.

24. A kit for detecting or quantifying a target nucleic acid on microarray, comprising:
a) a microarray solid support having a plurality of sample detection spots, wherein said sample detection spots are biomolecule probes complementary to a target nucleic acid;
b) a detectably-labeled nucleic acid probe complementary to a non-hybridized portion of a target nucleic acid that has hybridized to the biomolecule probe of (a); and
c) a solution comprising an RNase and a detection antibody specifically reactive with an RNA:DNA hybrid.

25. A kit for detecting or quantifying a target nucleic acid on microarray, comprising:
a) a nucleic acid probe complementary to a target nucleic acid;
b) a microarray solid support having a plurality of sample detection spots, wherein said sample detection spots are biomolecule probes complementary to a non-hybridized portion of the target nucleic acid after it has hybridized to the nucleic acid probe of (a); and
c) a solution comprising an RNase and a detection antibody specifically reactive with an RNA:DNA hybrid.

26. A kit for detecting or quantifying a target nucleic acid on microarray, comprising:
a) a microarray solid support having a plurality of sample detection spots, wherein said sample detection spots are biomolecule probes complementary to a target nucleic acid and biomolecules complementary to a detectably-labeled biomolecule probe;
b) a detectably-labeled biomolecule probe complementary to a solid-support bound biomolecule of (a); and
c) a solution comprising an RNase and a detection antibody specifically reactive with an RNA:DNA hybrid.

* * * * *